US012594409B2

(12) United States Patent
Juza et al.

(10) Patent No.: US 12,594,409 B2
(45) Date of Patent: Apr. 7, 2026

(54) SLEEVE FOR RETENTION OF A SURGICAL PORT COMPRISING FLANGES THAT ARE REVERSIBLY RADIALLY EXPANDABLE

(71) Applicant: UNIVERSITY HOSPITALS CLEVELAND MEDICAL CENTER, Cleveland, OH (US)

(72) Inventors: Ryan Juza, Cleveland, OH (US); Steve Schomisch, Cleveland, OH (US); Stephan Nieuwoudt, Cleveland, OH (US); Jeffrey Marks, Cleveland, OH (US)

(73) Assignee: UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 40 days.

(21) Appl. No.: 18/853,697

(22) PCT Filed: Apr. 3, 2024

(86) PCT No.: PCT/US2024/022776
§ 371 (c)(1),
(2) Date: Oct. 2, 2024

(87) PCT Pub. No.: WO2024/211371
PCT Pub. Date: Oct. 10, 2024

(65) Prior Publication Data
US 2025/0041578 A1 Feb. 6, 2025

Related U.S. Application Data

(60) Provisional application No. 63/493,873, filed on Apr. 3, 2023.

(51) Int. Cl.
*A61M 39/02* (2006.01)

(52) U.S. Cl.
CPC . *A61M 39/0247* (2013.01); *A61M 2039/0279* (2013.01)

(58) Field of Classification Search
CPC .......... A61M 25/04; A61M 2039/0261; A61B 2017/348; A61B 2017/3484
See application file for complete search history.

(56) References Cited

U.S. PATENT DOCUMENTS 1,719,428 A * 7/1929 Friedman ............ A61M 3/0291
604/105
5,203,773 A * 4/1993 Green .................... A61B 17/34
604/105

(Continued)

OTHER PUBLICATIONS

International Search Report and Written Opinion for PCT/US2024/022776, dated Jul. 12, 2024, pp. 1-19.

*Primary Examiner* — William R Carpenter
(74) *Attorney, Agent, or Firm* — EVENTIDE LAW LLC

(57) ABSTRACT

A sleeve for retention of a surgical port is disclosed. The sleeve comprises a first sleeve portion, a second sleeve portion, a plurality of flanges, and a reversible locking mechanism. The second sleeve portion is disposed around the first sleeve portion and is reversibly slidable distally from a first position to a second position along the first sleeve portion. The plurality of flanges is disposed in a radial sequence around the first sleeve portion. The flanges are radially collapsed along the first sleeve portion when the second sleeve portion is in the first position and are radially expanded when the second sleeve portion is in the second position. The first sleeve portion is configured for placement of a surgical port therethrough and to be fixedly secured to the surgical port therealong. Additional sleeves are also disclosed.

13 Claims, 27 Drawing Sheets

(56) References Cited

U.S. PATENT DOCUMENTS

| | | | | |
|---|---|---|---|---|
| 5,290,249 | A * | 3/1994 | Foster ................... | A61B 17/34 604/174 |
| 5,387,196 | A * | 2/1995 | Green ................... | A61B 17/34 606/167 |
| 5,431,676 | A * | 7/1995 | Dubrul .............. | A61B 17/3439 606/191 |
| 7,510,560 | B2 * | 3/2009 | Manzo .................. | A61B 17/12 606/153 |
| 8,287,503 | B2 * | 10/2012 | Albrecht ........... | A61B 17/3421 604/165.01 |
| 2001/0039430 | A1 | 11/2001 | Dubrul et al. | |
| 2002/0042622 | A1 | 4/2002 | Vargas et al. | |
| 2004/0199202 | A1 * | 10/2004 | Dubrul .................. | A61B 90/39 606/191 |
| 2005/0049667 | A1 | 3/2005 | Arbefeuille et al. | |
| 2010/0179567 | A1 | 7/2010 | Voss et al. | |

* cited by examiner 120    142    152    102

156

160

158

164

162

156

164

162

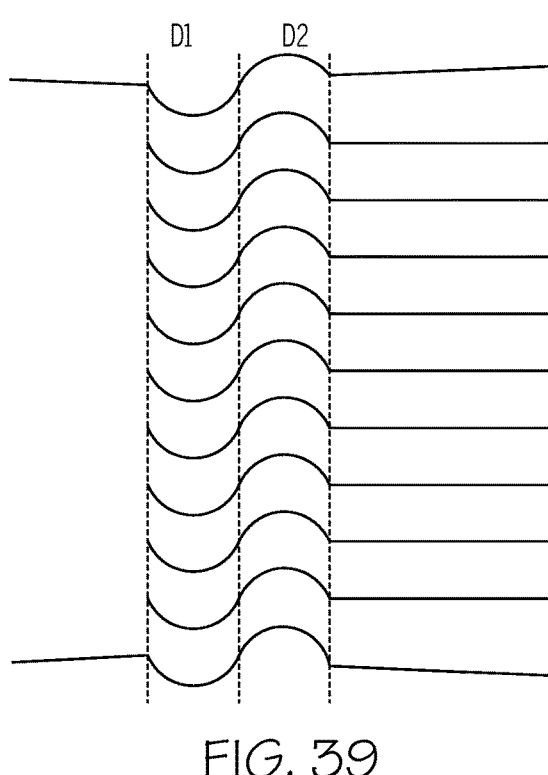
FIG. 39
| | Fully folded | | Half folded | |
|---|---|---|---|---|
| Ratio 1.0<br>D1 = 6mm<br>D2 = 6mm | | | | |
FIG. 40
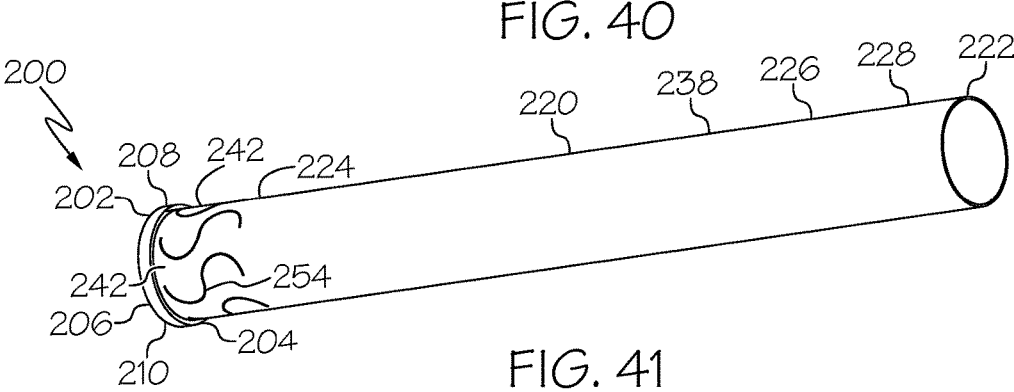
FIG. 41

SLEEVE FOR RETENTION OF A SURGICAL PORT COMPRISING FLANGES THAT ARE REVERSIBLY RADIALLY EXPANDABLE

REFERENCE TO RELATED APPLICATIONS

This application claims the benefit of U.S. Provisional Application No. 63/493,873, filed on Apr. 3, 2023, which is hereby incorporated by reference.

FIELD OF THE INVENTION

The present invention relates generally to sleeves for retention of surgical ports comprising flanges that are reversibly radially expandable.

BACKGROUND OF THE INVENTION

Surgical ports are used in a wide variety of laparoscopic and other surgical procedures for inserting surgical instruments through body walls of patients and into surgical cavities. Robotic surgery is increasingly being used for such procedures. Since FDA approval of the Intuitive Da Vinci Surgical Systems robotic surgical platform in 2000, this platform has experienced a growth in both sales and utilization for minimally invasive surgical procedures around the world. In 2021, an estimated 1.8 million robotic procedures were performed worldwide with a curve of up to 10% growth annually. The indications for robotic procedures have grown from initial applications in pelvic surgery, particularly urologic, gynecologic, and colorectal, to more recent thoracic, retroperitoneal, and abdominal wall procedures. The expanding nature of robotic surgery has led to modifications in the design of the Da Vinci Surgical Systems platform to enable multi-quadrant surgery and improved optics. The basic design of the proprietary robotic arms and proprietary trocars has largely remained unchanged, though.

Challenges arise when performing robotic surgeries in a small space within a surgical cavity, between layers of the abdominal wall, and/or in multiple quadrants of the abdomen of a patient. Surgical ports often need to be docked at steep angles during use of surgical instruments inserted through the surgical ports. When the distal end of a surgical port is flush with a body wall, tilting the surgical port can obscure its entry into a surgical cavity and can cause injury to adjacent tissues. Moreover, as a surgical port moves within an incision in a body wall, the robotic port can retract into muscular or subcutaneous layers, resulting in significant tissue trauma or insufflation directly into the tissues of these layers, leading to $CO_2$ retention, crepitus, and respiratory acidosis. These problems can be addressed to some extent by inserting surgical ports deep within surgical cavities, but this results in reduced forward working space for surgery, which is also problematic.

One approach for retaining surgical ports in patients during surgeries is use of a secondary port with a retention balloon that is inflated once the surgical port is in position in a patient. For robotic ports, this approach requires placing a secondary port through which the robotic port can be nested and docked. The secondary port must be larger than the robotic port. A standard robotic port has an outer diameter of 8 mm. Thus, applying this approach to robotic ports requires using a secondary port with an outer diameter of about 12 mm. Use of secondary ports of this size also requires making larger incisions in patients than would otherwise be needed. While incisions of 8 mm are sufficient for use of robotic ports alone, the use of larger secondary ports require incisions of at least 12 mm. Incisions of 10 mm or more are associated with increased rates of pain, infection, and hernia in patients, which is a drawback. Retention balloons also can take up substantial space within a surgical cavity. This decreases available working space within the surgical cavity, which also is a drawback.

Another approach for retaining surgical ports in patients during surgeries is the use of surgical ports containing ridges. The ridges are intended to prevent sliding of the surgical ports out of surgical cavities. Unfortunately, the use of ridges for this purpose has not been particularly effective as they cannot retract tissue and provide minimal retention force.

A need exists for a port retention device that can maintain a surgical port, such as a robotic surgical port, within a surgical cavity, for preventing the surgical port from retracting into the subcutaneous space, and for maintaining optimal working space within the surgical cavity.

SUMMARY OF THE INVENTION

A first sleeve for retention of a surgical port is disclosed. The first sleeve comprises:
  (a) a first sleeve portion comprising a proximal end, a distal end, and a first sleeve portion body extending therebetween;
  (b) a second sleeve portion comprising a proximal end, a distal end, and a second sleeve portion body extending therebetween, the second sleeve portion being disposed around the first sleeve portion and being reversibly slidable distally from a first position to a second position along the first sleeve portion;
  (c) a plurality of flanges disposed in a radial sequence around the first sleeve portion adjacent the distal end of the first sleeve portion, each flange having a proximal end, a distal end, and a flange strip extending therebetween, the proximal end of each flange extending from the distal end of the second sleeve portion in the radial sequence, the distal end of each flange extending from the distal end of the first sleeve portion in the radial sequence, and the flanges being radially collapsed along the first sleeve portion when the second sleeve portion is in the first position and being radially expanded around the first sleeve portion when the second sleeve portion is in the second position; and
  (d) a reversible locking mechanism that can be reversibly actuated to prevent the second sleeve portion from sliding along the first sleeve portion when the second sleeve portion is in the second position.

The first sleeve portion body has an outer surface, an inner surface, a proximal opening, a distal opening, and a lumen extending between the proximal and distal openings of the first sleeve portion body.

The second sleeve portion body has an outer surface, an inner surface, a proximal opening, a distal opening, and a lumen extending between the proximal and distal openings of the second sleeve portion body.

The inner surface of the second sleeve portion body is in slidable contact with the outer surface of the first sleeve portion body.

The first sleeve portion is configured for placement of a surgical port through the proximal opening of the first sleeve portion body and into the lumen of the first sleeve portion body to the distal opening of the first sleeve portion body and to be fixedly secured to the surgical port along the inner surface of the first sleeve portion body.

In some embodiments, the second sleeve portion is configured for placement of the first sleeve portion within the lumen of the second sleeve portion body through the proximal opening of the second sleeve portion body.

In some embodiments, the plurality of flanges consists of 5 to 25 flanges.

In some embodiments, each flange has a radial length of 1 to 15 mm when radially expanded around the first sleeve portion.

In some embodiments, each flange is integral to the first and second sleeve portions. Also in some embodiments, each flange is attached to the first and second sleeve portions.

In some embodiments, each flange has a sigmoidal shape.

In some embodiments, each flange has an intermediate portion between the proximal and distal ends of the flange and a width that decreases distally from the proximal end of the flange to the intermediate portion and that increases distally from the intermediate portion to the distal end of the flange.

In some embodiments, the first sleeve portion, the second sleeve portion, and the plurality of flanges are made from one or more of polyethylene terephthalate glycol, polycarbonate, or polystyrene.

In some embodiments, the first sleeve further comprises a flexible film covering the second sleeve portion and the plurality of flanges, the flexible film being adhered to the first sleeve portion at the distal end of the first sleeve portion and to the second sleeve portion along the outer surface of the second sleeve portion body, and the flexible film not being adhered to the plurality of flanges.

Also disclosed is a first system for retention of a surgical port. The system comprises:

(a) the first sleeve; and (b) a surgical port.

The first sleeve portion is fixedly secured to the surgical port along the inner surface of the first sleeve portion body.

Also disclosed is a method of use of the first sleeve in performing a surgery on a patient in need thereof. The method comprises steps of:

(1) securing the first sleeve to a surgical port fixedly along the inner surface of the first sleeve portion body;

(2) inserting the surgical port and the first sleeve through an incision in a body wall of the patient such that the flanges of the first sleeve extend into a surgical cavity of the patient, wherein during the inserting the second sleeve portion is in the first position and the flanges are radially collapsed along the first sleeve portion;

(3) sliding the second sleeve portion from the first position to the second position, thereby radially expanding the flanges around the first sleeve portion;

(4) actuating the reversible locking mechanism to prevent the second sleeve portion from sliding along the first sleeve portion; and (5) inserting one or more surgical instruments through the surgical port into the surgical cavity of the patient.

In some embodiments, the method further comprises steps of:

(6) withdrawing the one or more surgical instruments from the surgical cavity of the patient through the surgical port;

(7) releasing the reversible locking mechanism to allow the second sleeve portion to slide along the first sleeve portion;

(8) sliding the second sleeve portion from the second position to the first position, thereby radially collapsing the flanges along the first sleeve portion; and (9) withdrawing the surgical port and the first sleeve from the surgical cavity through the incision in the body wall.

Also disclosed is a second sleeve for retention of a surgical port. The second sleeve comprises:

(a) a first sleeve portion comprising a proximal end, a distal end, and a first sleeve portion body extending therebetween;

(b) a second sleeve portion comprising a proximal end, a distal end, and a second sleeve portion body extending therebetween, the second sleeve portion being disposed proximally to the first sleeve portion and being reversibly translatable distally from a first position to a second position toward the first sleeve portion;

(c) a plurality of flanges disposed in a radial sequence between the first sleeve portion and the second sleeve portion, each flange having a proximal end, a distal end, and a flange strip extending therebetween, the proximal end of each flange extending from the distal end of the second sleeve portion in the radial sequence, the distal end of each flange extending from the proximal end of the first sleeve portion in the radial sequence, and the flanges being radially collapsed when the second sleeve portion is in the first position and being radially expanded when the second sleeve portion is in the second position; and (d) a reversible locking mechanism that can be reversibly actuated to prevent the second sleeve portion from translating away from the first sleeve portion when the second sleeve portion is in the second position.

The first sleeve portion body has an outer surface, an inner surface, a proximal opening, a distal opening, and a lumen extending between the proximal and distal openings of the first sleeve portion body.

The second sleeve portion body has an outer surface, an inner surface, a proximal opening, a distal opening, and a lumen extending between the proximal and distal openings of the second sleeve portion body.

The second sleeve is configured for placement of a surgical port through the lumen of the second sleeve portion body and into the lumen of the first sleeve portion body to the distal opening of the first sleeve portion body, for the second sleeve to be fixedly secured to the surgical port along the inner surface of the first sleeve portion body, and for the inner surface of the second sleeve portion body to be in slidable contact with the surgical port.

In some embodiments, the plurality of flanges consists of 5 to 25 flanges.

In some embodiments, each flange has a radial length of 1 to 15 mm when radially expanded around the first sleeve portion.

In some embodiments, each flange is integral to the first and second sleeve portions. Also in some embodiments, each flange is attached to the first and second sleeve portions.

In some embodiments, each flange has a sigmoidal shape.

In some embodiments, each flange has an intermediate portion between the proximal and distal ends of the flange and a width that decreases distally from the proximal end of the flange to the intermediate portion and that increases distally from the intermediate portion to the distal end of the flange.

In some embodiments, the first sleeve portion, the second sleeve portion, and the plurality of flanges are made from one or more of polyethylene terephthalate glycol, polycarbonate, or polystyrene.

Also disclosed is a second system for retention of a surgical port. The second system comprises:

(a) the second sleeve; and (b) a surgical port.

The first sleeve portion is fixedly secured to the surgical port along the inner surface of the first sleeve portion body.

Also disclosed is a method of use of the second sleeve in performing a surgery on a patient in need thereof. The method comprises steps of:

(1) securing the second sleeve to a surgical port fixedly along the inner surface of the first sleeve portion body;

(2) inserting the surgical port and the second sleeve through an incision in a body wall of the patient such that the flanges of the sleeve extend into a surgical cavity of the patient, wherein during the inserting the second sleeve portion is in the first position and the flanges are radially collapsed;

(3) translating the second sleeve portion from the first position to the second position, thereby radially expanding the flanges;

(4) actuating the reversible locking mechanism to prevent the second sleeve portion from translating away from the first sleeve portion; and (5) inserting one or more surgical instruments through the surgical port into the surgical cavity of the patient.

In some embodiments, the method further comprises steps of:

(6) withdrawing the one or more surgical instruments from the surgical cavity of the patient through the surgical port;

(7) releasing the reversible locking mechanism to allow the second sleeve portion to translate away from the first sleeve portion;

(8) translating the second sleeve portion from the second position to the first position, thereby radially collapsing the flanges; and (9) withdrawing the surgical port and the second sleeve from the surgical cavity through the incision in the body wall.

Also disclosed is a third sleeve for retention of a surgical port. The third sleeve comprises:

(a) a first sleeve portion comprising a proximal end, a distal end, and a first sleeve portion body extending therebetween;

(b) a second sleeve portion comprising a proximal end, a distal end, and a second sleeve portion body extending therebetween, the second sleeve portion being disposed proximally to the first sleeve portion, and the first sleeve portion being reversibly translatable proximally from a distal position to a proximal position toward the second sleeve portion;

(c) a plurality of flanges disposed in a radial sequence between the first sleeve portion and the second sleeve portion, each flange having a proximal end, a distal end, and a flange strip extending therebetween, the proximal end of each flange extending from the distal end of the second sleeve portion in the radial sequence, the distal end of each flange extending from the proximal end of the first sleeve portion in the radial sequence, and the flanges being radially collapsed when the first sleeve portion is in the distal position and being radially expanded when the first sleeve portion is in the proximal position; and (d) a reversible locking mechanism that can be reversibly actuated to prevent the first sleeve portion from translating away from the second sleeve portion when the first sleeve portion is in the proximal position.

The first sleeve portion body has an outer surface, an inner surface, a proximal opening, a distal opening, and a lumen extending between the proximal and distal openings of the first sleeve portion body.

The second sleeve portion body has an outer surface, an inner surface, a proximal opening, a distal opening, and a lumen extending between the proximal and distal openings of the second sleeve portion body.

The second sleeve portion is configured for placement of a surgical port into the lumen of the second sleeve portion body and to be fixedly secured to the surgical port along the inner surface of the second sleeve portion body.

In some embodiments, the sleeve further comprises one or more retraction cables attached to the first sleeve portion at the distal end of the first sleeve portion for translating the first sleeve portion from the distal position to the proximal position.

In some embodiments the plurality of flanges consists of 5 to 25 flanges.

In some embodiments, each flange has a radial length of 1 to 15 mm when radially expanded around the first sleeve portion.

In some embodiments, each flange is integral to the first and second sleeve portions. Also in some embodiments, each flange is attached to the first and second sleeve portions.

In some embodiments, each flange has a sigmoidal shape.

In some embodiments, each flange has an intermediate portion between the proximal and distal ends of the flange and a width that decreases distally from the proximal end of the flange to the intermediate portion and that increases distally from the intermediate portion to the distal end of the flange.

In some embodiments, the first sleeve portion, the second sleeve portion, and the plurality of flanges are made from one or more of polyethylene terephthalate glycol, polycarbonate, or polystyrene.

Also disclosed is a third system for retention of a surgical port. The third system comprises:

(a) the third sleeve; and (b) a surgical port.

The second sleeve portion is fixedly secured to the surgical port along the inner surface of the second sleeve portion body.

Also disclosed is a method of use of the third sleeve in performing a surgery on a patient in need thereof. The method comprises steps of:

(1) securing the third sleeve to a surgical port fixedly along the inner surface of the second sleeve portion body;

(2) inserting the surgical port and the third sleeve through an incision in a body wall of the patient such that the flanges of the sleeve extend into a surgical cavity of the patient, wherein during the inserting the first sleeve portion is in the distal position and the flanges are radially collapsed;

(3) translating the first sleeve portion from the distal position to the proximal position, thereby radially expanding the flanges;

(4) actuating the reversible locking mechanism to prevent the first sleeve portion from translating away from the second sleeve portion; and (5) inserting one or more surgical instruments through the surgical port into the surgical cavity of the patient.

In some embodiments, the method further comprises steps of:

(6) withdrawing the one or more surgical instruments from the surgical cavity of the patient through the surgical port;

(7) releasing the reversible locking mechanism to allow the first sleeve portion to translate away from the second sleeve portion;

(8) translating the first sleeve portion from the proximal position to the distal position, thereby radially collapsing the flanges; and (9) withdrawing the surgical port and the third sleeve from the surgical cavity through the incision in the body wall.

Example embodiments include the following:

Embodiment 1: A sleeve for retention of a surgical port comprising:

(a) a first sleeve portion comprising a proximal end, a distal end, and a first sleeve portion body extending therebetween;

(b) a second sleeve portion comprising a proximal end, a distal end, and a second sleeve portion body extending therebetween, the second sleeve portion being disposed around the first sleeve portion and being reversibly slidable distally from a first position to a second position along the first sleeve portion;

(c) a plurality of flanges disposed in a radial sequence around the first sleeve portion adjacent the distal end of the first sleeve portion, each flange having a proximal end, a distal end, and a flange strip extending therebetween, the proximal end of each flange extending from the distal end of the second sleeve portion in the radial sequence, the distal end of each flange extending from the distal end of the first sleeve portion in the radial sequence, and the flanges being radially collapsed along the first sleeve portion when the second sleeve portion is in the first position and being radially expanded around the first sleeve portion when the second sleeve portion is in the second position; and (d) a reversible locking mechanism that can be reversibly actuated to prevent the second sleeve portion from sliding along the first sleeve portion when the second sleeve portion is in the second position, wherein:

the first sleeve portion body has an outer surface, an inner surface, a proximal opening, a distal opening, and a lumen extending between the proximal and distal openings of the first sleeve portion body;

the second sleeve portion body has an outer surface, an inner surface, a proximal opening, a distal opening, and a lumen extending between the proximal and distal openings of the second sleeve portion body;

the inner surface of the second sleeve portion body is in slidable contact with the outer surface of the first sleeve portion body; and the first sleeve portion is configured for placement of a surgical port through the proximal opening of the first sleeve portion body and into the lumen of the first sleeve portion body to the distal opening of the first sleeve portion body and to be fixedly secured to the surgical port along the inner surface of the first sleeve portion body.

Embodiment 2: The sleeve according to embodiment 1, wherein the second sleeve portion is configured for placement of the first sleeve portion within the lumen of the second sleeve portion body through the proximal opening of the second sleeve portion body.

Embodiment 3: The sleeve according to embodiment 1 or embodiment 2, wherein the plurality of flanges consists of 5 to 25 flanges.

Embodiment 4: The sleeve according to any one of embodiments 1 to 3, wherein each flange has a radial length of 1 to 15 mm when radially expanded around the first sleeve portion.

Embodiment 5: The sleeve according to any one of embodiments 1 to 4, wherein each flange is integral to the first and second sleeve portions.

Embodiment 6: The sleeve according to any one of embodiments 1 to 4, wherein each flange is attached to the first and second sleeve portions.

Embodiment 7: The sleeve according to any one of embodiments 1 to 6, wherein each flange has a sigmoidal shape.

Embodiment 8: The sleeve according to any one of embodiments 1 to 7, wherein each flange has an intermediate portion between the proximal and distal ends of the flange and a width that decreases distally from the proximal end of the flange to the intermediate portion and that increases distally from the intermediate portion to the distal end of the flange.

Embodiment 9: The sleeve according to any one of embodiments 1 to 8, wherein the first sleeve portion, the second sleeve portion, and the plurality of flanges are made from one or more of polyethylene terephthalate glycol, polycarbonate, or polystyrene.

Embodiment 10: The sleeve according to any one of embodiments 1 to 9, further comprising a flexible film covering the second sleeve portion and the plurality of flanges, the flexible film being adhered to the first sleeve portion at the distal end of the first sleeve portion and to the second sleeve portion along the outer surface of the second sleeve portion body, and the flexible film not being adhered to the plurality of flanges.

Embodiment 11: A system for retention of a surgical port comprising:

(a) the sleeve according to any one of embodiments 1 to 10; and (b) a surgical port, wherein:

the first sleeve portion is fixedly secured to the surgical port along the inner surface of the first sleeve portion body.

Embodiment 12: A method of use of the sleeve of any one of embodiments 1 to 10 in performing a surgery on a patient in need thereof, the method comprising steps of:

(1) securing the sleeve to a surgical port fixedly along the inner surface of the first sleeve portion body;

(2) inserting the surgical port and the sleeve through an incision in a body wall of the patient such that the flanges of the sleeve extend into a surgical cavity of the patient, wherein during the inserting the second sleeve portion is in the first position and the flanges are radially collapsed along the first sleeve portion;

(3) sliding the second sleeve portion from the first position to the second position, thereby radially expanding the flanges around the first sleeve portion;

(4) actuating the reversible locking mechanism to prevent the second sleeve portion from sliding along the first sleeve portion; and (5) inserting one or more surgical instruments through the surgical port into the surgical cavity of the patient.

Embodiment 13: The method according to embodiment 12, the method further comprising steps of:

(6) withdrawing the one or more surgical instruments from the surgical cavity of the patient through the surgical port;

(7) releasing the reversible locking mechanism to allow the second sleeve portion to slide along the first sleeve portion;

(8) sliding the second sleeve portion from the second position to the first position, thereby radially collapsing the flanges along the first sleeve portion; and (9) withdrawing the surgical port and the sleeve from the surgical cavity through the incision in the body wall.

Embodiment 14: A sleeve for retention of a surgical port comprising:

(a) a first sleeve portion comprising a proximal end, a distal end, and a first sleeve portion body extending therebetween;

(b) a second sleeve portion comprising a proximal end, a distal end, and a second sleeve portion body extending therebetween, the second sleeve portion being disposed proximally to the first sleeve portion and being reversibly translatable distally from a first position to a second position toward the first sleeve portion;

(c) a plurality of flanges disposed in a radial sequence between the first sleeve portion and the second sleeve portion, each flange having a proximal end, a distal end, and a flange strip extending therebetween, the proximal end of each flange extending from the distal end of the second sleeve portion in the radial sequence, the distal end of each flange extending from the proximal end of the first sleeve portion in the radial sequence, and the flanges being radially collapsed when the second sleeve portion is in the first position and being radially expanded when the second sleeve portion is in the second position; and (d) a reversible locking mechanism that can be reversibly actuated to prevent the second sleeve portion from translating away from the first sleeve portion when the second sleeve portion is in the second position, wherein:

the first sleeve portion body has an outer surface, an inner surface, a proximal opening, a distal opening, and a lumen extending between the proximal and distal openings of the first sleeve portion body;

the second sleeve portion body has an outer surface, an inner surface, a proximal opening, a distal opening, and a lumen extending between the proximal and distal openings of the second sleeve portion body; and the sleeve is configured for placement of a surgical port through the lumen of the second sleeve portion body and into the lumen of the first sleeve portion body to the distal opening of the first sleeve portion body, for the sleeve to be fixedly secured to the surgical port along the inner surface of the first sleeve portion body, and for the inner surface of the second sleeve portion body to be in slidable contact with the surgical port.

Embodiment 15: The sleeve according to embodiment 14, wherein the plurality of flanges consists of 5 to 25 flanges.

Embodiment 16: The sleeve according to embodiment 14 or embodiment 15, wherein each flange has a radial length of 1 to 15 mm when radially expanded around the first sleeve portion.

Embodiment 17: The sleeve according to any one of embodiments 14 to 16, wherein each flange is integral to the first and second sleeve portions.

Embodiment 18: The sleeve according to any one of embodiments 14 to 16, wherein each flange is attached to the first and second sleeve portions.

Embodiment 19: The sleeve according to any one of embodiments 14 to 18, wherein each flange has a sigmoidal shape.

Embodiment 20: The sleeve according to any one of embodiments 14 to 19, wherein each flange has an intermediate portion between the proximal and distal ends of the flange and a width that decreases distally from the proximal end of the flange to the intermediate portion and that increases distally from the intermediate portion to the distal end of the flange.

Embodiment 21: The sleeve according to any one of embodiments 14 to 20, wherein the first sleeve portion, the second sleeve portion, and the plurality of flanges are made from one or more of polyethylene terephthalate glycol, polycarbonate, or polystyrene.

Embodiment 22: A system for retention of a surgical port comprising:

(a) the sleeve according to any one of embodiments 14 to 21; and (b) a surgical port, wherein:

the first sleeve portion is fixedly secured to the surgical port along the inner surface of the first sleeve portion body.

Embodiment 23: A method of use of the sleeve according to any one of embodiments 14 to 21 in performing a surgery on a patient in need thereof, the method comprising steps of:

(1) securing the sleeve to a surgical port fixedly along the inner surface of the first sleeve portion body;

(2) inserting the surgical port and the sleeve through an incision in a body wall of the patient such that the flanges of the sleeve extend into a surgical cavity of the patient, wherein during the inserting the second sleeve portion is in the first position and the flanges are radially collapsed;

(3) translating the second sleeve portion from the first position to the second position, thereby radially expanding the flanges;

(4) actuating the reversible locking mechanism to prevent the second sleeve portion from translating away from the first sleeve portion; and (5) inserting one or more surgical instruments through the surgical port into the surgical cavity of the patient.

Embodiment 24: The method according to embodiment 23, the method further comprising steps of:

(6) withdrawing the one or more surgical instruments from the surgical cavity of the patient through the surgical port;

(7) releasing the reversible locking mechanism to allow the second sleeve portion to translate away from the first sleeve portion;

(8) translating the second sleeve portion from the second position to the first position, thereby radially collapsing the flanges; and (9) withdrawing the surgical port and the sleeve from the surgical cavity through the incision in the body wall.

Embodiment 25: A sleeve for retention of a surgical port comprising:

(a) a first sleeve portion comprising a proximal end, a distal end, and a first sleeve portion body extending therebetween;

(b) a second sleeve portion comprising a proximal end, a distal end, and a second sleeve portion body extending therebetween, the second sleeve portion being disposed proximally to the first sleeve portion, and the first sleeve portion being reversibly translatable proximally from a distal position to a proximal position toward the second sleeve portion;

(c) a plurality of flanges disposed in a radial sequence between the first sleeve portion and the second sleeve portion, each flange having a proximal end, a distal end, and a flange strip extending therebetween, the proximal end of each flange extending from the distal end of the second sleeve portion in the radial sequence, the distal end of each flange extending from the proximal end of the first sleeve portion in the radial sequence, and the flanges being radially collapsed when the first sleeve portion is in the distal position and being radially expanded when the first sleeve portion is in the proximal position; and (d) a reversible locking mechanism that can be reversibly actuated to prevent the first sleeve portion from translating away from the second sleeve portion when the first sleeve portion is in the proximal position, wherein:

the first sleeve portion body has an outer surface, an inner surface, a proximal opening, a distal opening, and a lumen extending between the proximal and distal openings of the first sleeve portion body;

the second sleeve portion body has an outer surface, an inner surface, a proximal opening, a distal opening, and a lumen extending between the proximal and distal openings of the second sleeve portion body;

the second sleeve portion is configured for placement of a surgical port into the lumen of the second sleeve portion body and to be fixedly secured to the surgical port along the inner surface of the second sleeve portion body.

Embodiment 26: The sleeve according to embodiment 25, further comprising one or more retraction cables attached to the first sleeve portion at the distal end of the first sleeve portion for translating the first sleeve portion from the distal position to the proximal position.

Embodiment 27: The sleeve according to embodiment 25 or embodiment 26, wherein the plurality of flanges consists of 5 to 25 flanges.

Embodiment 28: The sleeve according to any one of embodiments 25 to 27, wherein each flange has a radial length of 1 to 15 mm when radially expanded around the first sleeve portion.

Embodiment 29: The sleeve according to any one of embodiments 25 to 28, wherein each flange is integral to the first and second sleeve portions.

Embodiment 30: The sleeve according to any one of embodiments 25 to 29, wherein each flange is attached to the first and second sleeve portions.

Embodiment 31: The sleeve according to any one of embodiments 25 to 30, wherein each flange has a sigmoidal shape.

Embodiment 32: The sleeve according to any one of embodiments 25 to 31, wherein each flange has an intermediate portion between the proximal and distal ends of the flange and a width that decreases distally from the proximal end of the flange to the intermediate portion and that increases distally from the intermediate portion to the distal end of the flange.

Embodiment 33: The sleeve according to any one of embodiments 25 to 32, wherein the first sleeve portion, the second sleeve portion, and the plurality of flanges are made from one or more of polyethylene terephthalate glycol, polycarbonate, or polystyrene.

Embodiment 34: A system for retention of a surgical port comprising:

(a) the sleeve according to any one of embodiments 25 to 33; and (b) a surgical port, wherein:

the second sleeve portion is fixedly secured to the surgical port along the inner surface of the second sleeve portion body.

Embodiment 35: A method of use of the sleeve according to any one of embodiments 25 to 33 in performing a surgery on a patient in need thereof, the method comprising steps of:

(1) securing the sleeve to a surgical port fixedly along the inner surface of the second sleeve portion body;

(2) inserting the surgical port and the sleeve through an incision in a body wall of the patient such that the flanges of the sleeve extend into a surgical cavity of the patient, wherein during the inserting the first sleeve portion is in the distal position and the flanges are radially collapsed;

(3) translating the first sleeve portion from the distal position to the proximal position, thereby radially expanding the flanges;

(4) actuating the reversible locking mechanism to prevent the first sleeve portion from translating away from the second sleeve portion; and (5) inserting one or more surgical instruments through the surgical port into the surgical cavity of the patient.

Embodiment 36: The method according to embodiment 35, the method further comprising steps of:

(6) withdrawing the one or more surgical instruments from the surgical cavity of the patient through the surgical port;

(7) releasing the reversible locking mechanism to allow the first sleeve portion to translate away from the second sleeve portion;

(8) translating the first sleeve portion from the proximal position to the distal position, thereby radially collapsing the flanges; and (9) withdrawing the surgical port and the sleeve from the surgical cavity through the incision in the body wall.

BRIEF DESCRIPTION OF THE DRAWINGS

FIG. 39 shows a schematic view of folding lines D1 and D2 of the cutout of FIG. 19.

FIG. 40 shows the resulting shapes of the flanges of a first sleeve as described herein with sigmoid-shaped cuts made from the cut out of FIG. 19 when the flanges are fully radially expanded or partially radially expanded.

FIG. 41 is a perspective view of a first sleeve portion, a second sleeve portion, and a plurality of flanges of the second sleeve as described herein. Like the first sleeve, the second sleeve also comprises a reversible locking mechanism, which is not shown in FIG. 41, but which can be like the reversible locking mechanism shown in FIGS. 20-23. As shown, the second sleeve portion is in the first position and the flanges are radially collapsed.

DETAILED DESCRIPTION OF THE INVENTION

Figures 1, 2, 3:
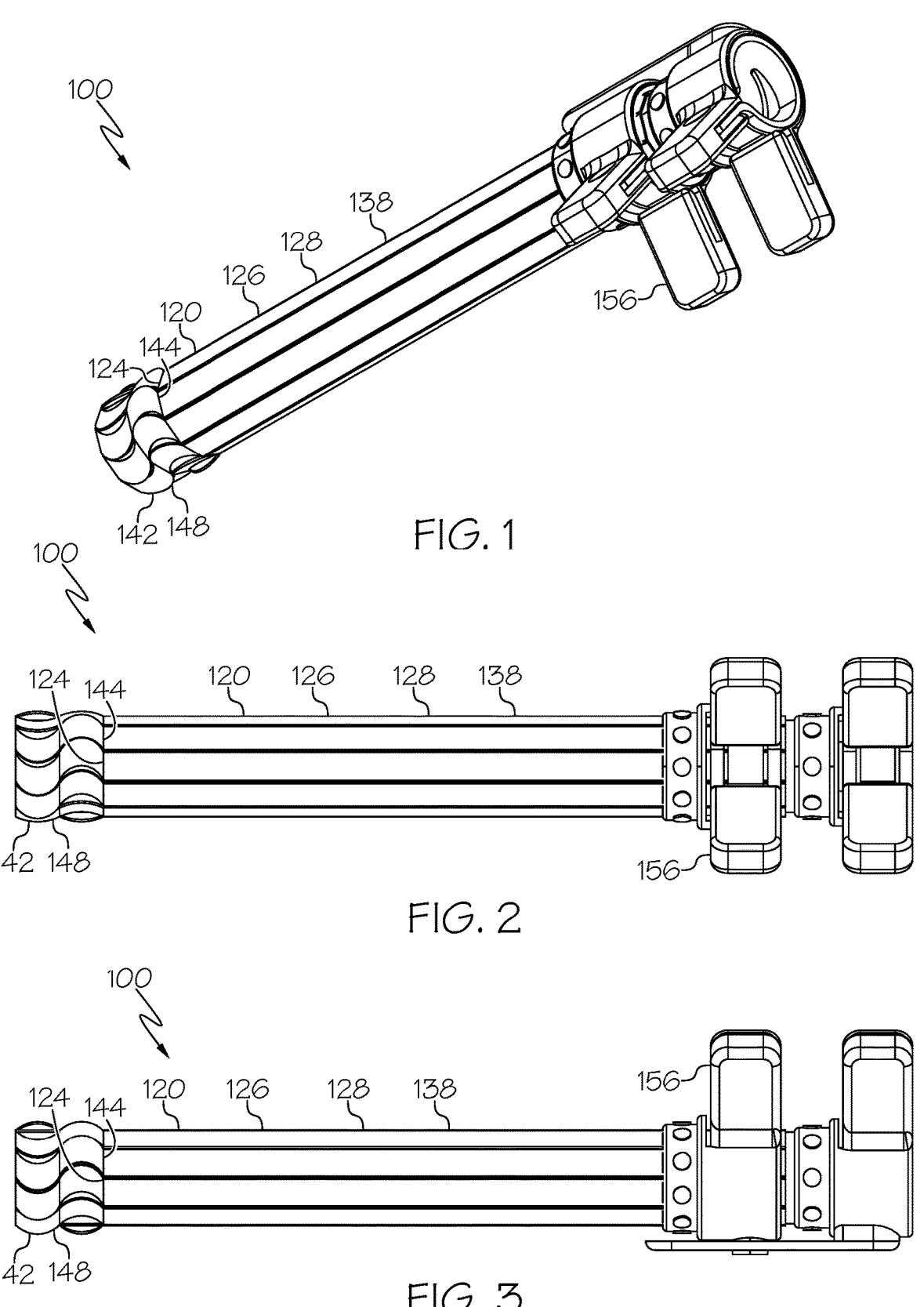
FIG. 1 is a perspective view of an exemplary first sleeve for retention of a surgical port as described herein comprising a first sleeve portion, a second sleeve portion, a plurality of flanges, and a reversible locking mechanism. As shown, the second sleeve portion is in the first position and the flanges are radially collapsed.
FIG. 2 is a side view of the sleeve of FIG. 1.
FIG. 3 is a top view of the sleeve of FIG. 1.
Figure 4:
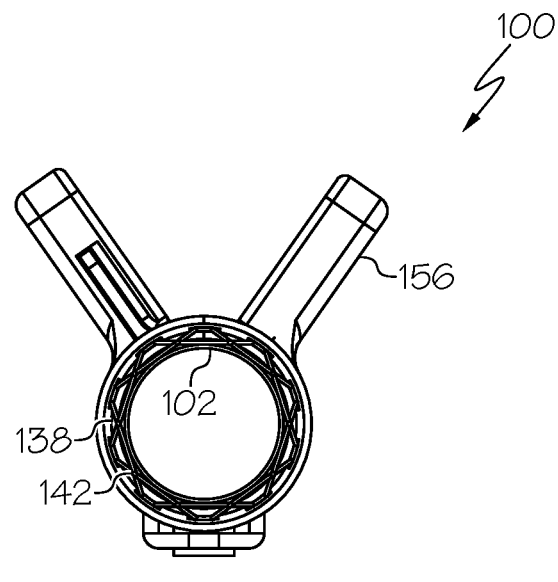
FIG. 4 is a front view of the sleeve of FIG. 1.
Figure 5:
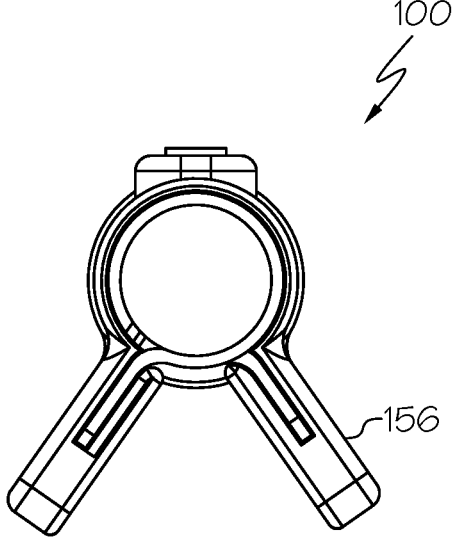
FIG. 5 is a back view of the sleeve of FIG. 1.

We have developed various sleeves for retention of surgical ports. The sleeves vary with respect to their structures and configurations but each is useful for maintaining a surgical port, such as a robotic surgical port, within a surgical cavity, for preventing the surgical port from retracting into the subcutaneous space, and for maintaining optimal working space within the surgical cavity.

As shown in FIGS. 1-10, a first sleeve 100 for retention of a surgical port 500 is provided. As described in detail below, during use the sleeve 100 is attached to an outer surface 502 of a surgical port 500 and includes flanges 142 that are reversibly radially expandable, allowing insertion of the surgical port 500 through an incision in a body wall of a patient into a surgical cavity of the patient when the flanges 142 are radially collapsed, and retention of the surgical port 500 within the surgical cavity when the flanges 142 are radially expanded. The flanges 142 of the sleeve 100 can be used to retract tissue of the surgical cavity adjacent the flanges 142, preventing the tissue from sliding over a distal opening of the surgical port 500 and interfering with use of the surgical instruments through the surgical port 500, and deflect fluids from dripping over the lens of the surgical camera. The sleeve 100 also allows maintaining insufflation via a surgical port 500 at steeper surgical angles than are achievable with use of retention balloons and more reliably than in the absence of a device for retention. The sleeve 100 also allows a surgical port 500 to be supported by the body wall of a patient while being retained within a surgical cavity without need for a surgeon to constantly hold and guide the surgical port 500. The sleeve 100 also contributes minimally to the outer diameter of the surgical port 500, thus minimizing the increase in the incision size needed for port insertion. The sleeve 100 thus allows safer and easier use of surgical ports.

With reference to FIGS. 11-18, the sleeve 100 comprises a first sleeve portion 102 comprising a proximal end 104, a distal end 106, and a first sleeve portion body 108 extending therebetween. The first sleeve portion body 108 has an outer surface 110, an inner surface 112, a proximal opening 114, a distal opening 116, and a lumen 118 extending between the proximal and distal openings 114, 116 of the first sleeve portion body 108. The first sleeve portion 102 is configured for placement of a surgical port 500 through the proximal opening 114 of the first sleeve portion body 108 and into the lumen 118 of the first sleeve portion body 108 to the distal opening 116 of the first sleeve portion body 108 and to be fixedly secured to the surgical port 500 along the inner surface of the first sleeve portion body 112. This configuration can be accomplished, for example, based on the first sleeve portion 102 and the surgical port 500 having a complementary fit.

The first sleeve portion 102 can have proportions including an axial length substantially greater than its diameter, like a tube, or an axial length substantially less than its diameter, like a collar, or an axial length that is neither substantially greater than, nor less than, its diameter, among other proportions. A first sleeve portion 102 having an axial length substantially greater than its diameter is shown in FIGS. 11-18. A first sleeve portion 102 having an axial length that is neither substantially greater than, nor less than, its diameter is shown in FIGS. 47-51.

In some embodiments, the first sleeve portion 102 can be made, for example, from one or more of polyethylene terephthalate glycol, polycarbonate, or polystyrene. This can be advantageous as the resulting first sleeve portion 102 can be semi-rigid, thus allowing the first sleeve portion 102 to be sufficiently rigid that tissues of the patient will not cause the first sleeve portion 102 to collapse during placement and use in the patient. This also can be advantageous for preventing the first sleeve portion 102 from damaging tissues of the patient. This also can be advantageous because these materials are biocompatible for transient contact and are sterilizable.

With reference to FIGS. 11-18, the sleeve 100 also comprises a second sleeve portion 120 comprising a proximal end 122, a distal end 124, and a second sleeve portion body 126 extending therebetween. The second sleeve portion body 126 has an outer surface 128, an inner surface 130, a proximal opening 132, a distal opening 134, and a lumen 136 extending between the proximal and distal openings 132, 134 of the second sleeve portion body 126. The inner surface 130 of the second sleeve portion body 126 is in slidable contact with the outer surface 110 of the first sleeve portion body 108.

The second sleeve portion 120 is disposed around the first sleeve portion 102 and is reversibly slidable distally from a first position 138 to a second position 140 along the first sleeve portion 102.

The second sleeve portion 120 can have proportions including an axial length substantially greater than its diameter, like a tube, among other proportions.

Like the first sleeve portion 102, in some embodiments the second sleeve portion 120 can be made, for example, from one or more of polyethylene terephthalate glycol, polycarbonate, or polystyrene. This can be advantageous as the resulting second sleeve portion 120 can be semi-rigid, also allowing the second sleeve portion 120 to be sufficiently rigid that tissues of the patient will not cause the second sleeve portion 120 to collapse during placement and use in the patient. This also can be advantageous for preventing the second sleeve portion 120 from damaging tissues of the patient. Also, as noted, these materials are biocompatible for transient contact and are sterilizable.

In some embodiments, the second sleeve portion 120 is configured for placement of the first sleeve portion 102 within the lumen 136 of the second sleeve portion body 126 through the proximal opening 132 of the second sleeve portion body 126. This configuration can be accomplished, for example, based on first sleeve portion 102 and the second sleeve portion 120 being only semi-rigid, and thus sufficiently flexible for placement of the first sleeve portion 102 within the lumen 136 of the second sleeve portion body 126 through the proximal opening 132 of the second sleeve portion body 126.

With reference to FIGS. 11-18, the sleeve 100 also comprises a plurality of flanges 142 disposed in a radial sequence around the first sleeve portion 102 adjacent to the distal end 106 of the first sleeve portion 102. Each flange 142 has a proximal end 144, a distal end 146, and a flange strip 148 extending therebetween. The proximal end 144 of each flange 142 extends from the distal end 124 of the second sleeve portion 120 in the radial sequence. The distal end 146 of each flange 142 extends from the distal end 106 of the first sleeve portion 102 in the radial sequence. As shown in FIGS. 1-5 and FIGS. 11-14, the flanges 142 are radially collapsed along the first sleeve portion 102 when the second sleeve portion 120 is in the first position 138. In contrast, as shown in FIGS. 6-10 and FIGS. 15-18, the flanges 142 are radially expanded around the first sleeve portion 102 when the second sleeve portion 120 is in the second position 140.

With reference to FIGS. 1-5 and FIGS. 11-14, when the second sleeve portion 120 is in the first position 138 and the flanges 142 are radially collapsed, the flanges 142 lie axially along the outer surface 110 of the first sleeve portion body 108, preferably flush against the outer surface 110 of the first sleeve portion body 108. The sleeve 100 is thin, such that the outer diameter of the sleeve 100, including the flanges 142 when radially collapsed, is only up to about 1.0 mm greater than the outer diameter of the surgical port 500 inserted therethrough. This is accomplished by making the first sleeve portion 102, the second sleeve portion 120, and the flanges 142 thin, for example based on each being made from a thin film having a thickness only up to about 0.5 mm, and thus contributing only up to about 1.0 mm in thickness to the outer diameter. This allows the sleeve 100 and a surgical port 500 therein to be inserted through an incision that is sized based essentially on the outer diameter of the surgical port 500, rather than needing to be sized, for example, based on the outer diameter of a substantially larger secondary external port. For example, for a robotic port having an outer diameter of 8 mm, the sleeve 100 and the robotic port therein can be inserted through an incision of approximately 8 to 9 mm into a surgical cavity. This avoids the need to use incisions of 10 mm or more, which as noted above, are associated with increased rates of pain, infection, and hernia in patients.

With reference to FIGS. 6-10 and FIGS. 15-18, when the second sleeve portion 120 is reversibly slidably moved distally to the second position 140 the flanges 142 become radially expanded. This occurs based on the second sleeve portion 120 pushing the flange strips 148 distally toward the distal end 106 of the first sleeve portion 102. Because the distal end 146 of each flange 142 extends from the distal end 106 of the first sleeve portion 102, this movement causes the flanges 142 to fold and extend radially from the outer surface 110 of the first sleeve portion body 108, collectively forming a retainer. The outer diameter of the sleeve 100 at the radially expanded flanges 142 becomes substantially greater than the outer diameter of the first sleeve portion 102 thereunder. This prevents the tip edges of a surgical port 500 within the sleeve 100 from being able to exit a surgical cavity of a patient, allows retraction of tissue from the tip of a surgical port 500 at steep angles within the surgical cavity providing more space for use of surgical tools inserted into the surgical cavity through the surgical port 500 than has been possible conventionally, and prevents insufflation tracking into a body wall of the patient. Upon partial withdrawal of a sleeve 100 and surgical port 500 from a surgical cavity through an incision, the radially expanded flanges 142 of the sleeve 100 contact tissue of the surgical cavity adjacent the incision, preventing further withdrawal of the sleeve 100 and surgical port 500. This allows the sleeve 100 to retain the surgical port 500 in the patient, even against further force.

Importantly, radial expansion of the flanges 142 is reversible based on sliding of the second sleeve portion 120 proximally from the second position 140 to the first position 138. This allows easy withdrawal of the sleeve 100 and a surgical port 500 therein from the surgical cavity of the patient, by way of the incision, without injury to tissue of the surgical cavity, and thus allows easy removal of the sleeve 100 and surgical port 500 from the patient.

As noted above, during use the sleeve 100 is attached to the outer surface 502 of a surgical port 500. This can be accomplished, for example, by friction and/or a reversible locking mechanism, as discussed below. In some embodiments the sleeve 100 is attached to the outer surface 502 of a surgical port 500 prior to placement in a patient. In accordance with these embodiments, the sleeve 100 and the surgical port 500 can be placed simultaneously in the patient in the standard method of port placement with no alterations made for the addition of the sleeve 100. Also in some embodiments the sleeve 100 is attached to the outer surface 502 of a surgical port 500 after placement in a patient. In accordance with these embodiments, the sleeve 100 can be placed in the patient first, followed by placement of the surgical port 500 through the sleeve 100, with the sleeve 100 becoming attached to the outer surface 502 of the surgical port 500 then. In any case, the sleeve 100 must be attached to the surgical port 500 prior to and during application of mechanical forces to prevent inadvertent sliding of the sleeve 100 relative to the surgical port 500. The sleeve 100 is generally attached such that the distal end of the sleeve 100 is aligned with the distal end of the surgical port 500. However, the sleeve 100 may be attached in other locations relative to the surgical port 500. For example, the sleeve 100 may be attached with the surgical port 500 extending 1, 2, 3, 4 or 5 mm beyond the distal end of the sleeve 100, if found to be advantageous by the user.

In some embodiments, the plurality of flanges 142 consists of 5 to 25 flanges. For example, in some embodiments the plurality of flanges 142 consists of 6 to 20 flanges, 7 to 17 flanges, or 8 to 15 flanges, among other ranges. Also in some embodiments the plurality of flanges 142 consists of 5, 6, 7, 8, 9, 10, 11, 12, 13, 14, 15, 16, 17, 18, 19, 20, 21, 22, 23, 24, or 25 flanges. Making the sleeve 100 with a relatively low number of flanges 142, e.g., 5 to 8 flanges, can be advantageous for promoting rigidity of the flanges 142. Making the sleeve 100 with a relatively high number of flanges 142, e.g., 15 to 25 flanges, can be advantageous for providing the flanges 142 with a more rounded shape when folded, reducing the sharpness of their edges and reducing open spaces between adjacent flanges 142.

Figures 6, 7, 8:
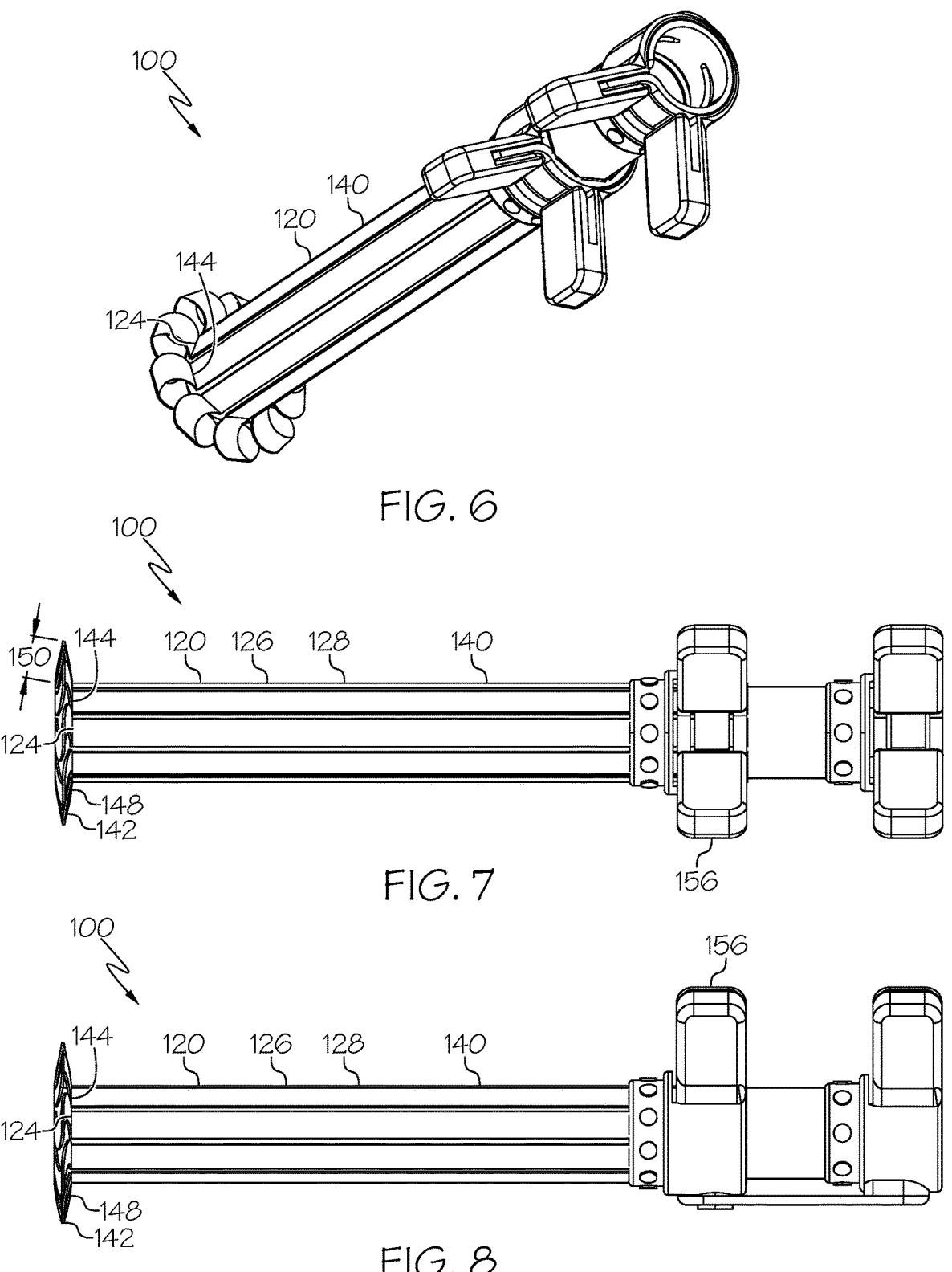
FIG. 6 is a perspective view of the sleeve of FIG. 1. As shown, the second sleeve portion is in the second position and the flanges are radially expanded.
FIG. 7 is a side view of the sleeve of FIG. 6.
FIG. 8 is a top view of the sleeve of FIG. 6.
Figures 9, 10:
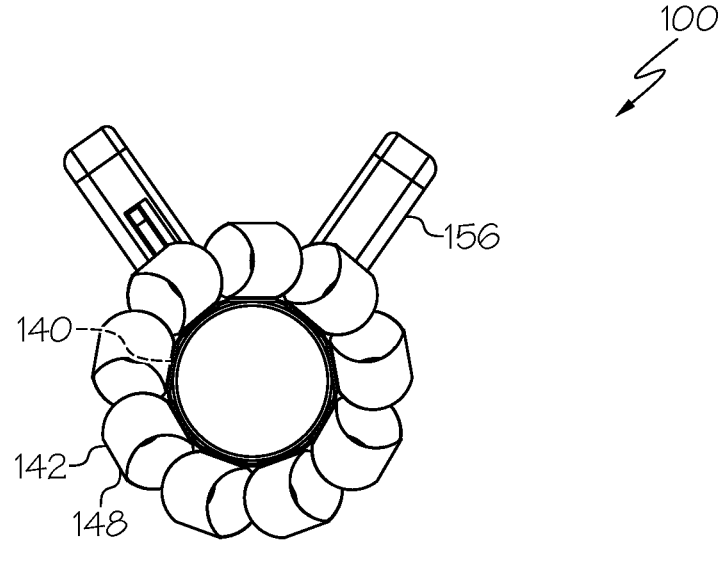
FIG. 9 is a front view of the sleeve of FIG. 6.
FIG. 10 is a back view of the sleeve of FIG. 6.
Figure 11:
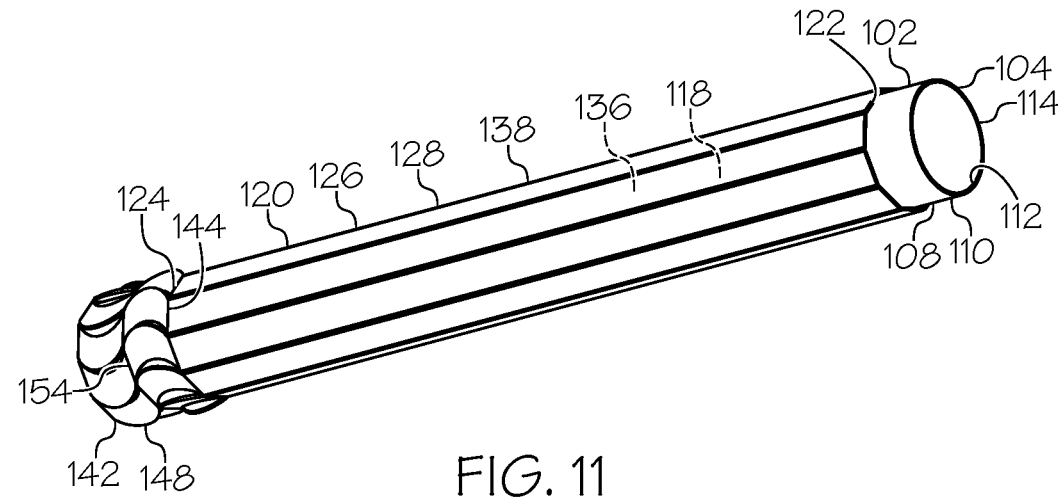
FIG. 11 is a first perspective view of the first sleeve portion, the second sleeve portion, the plurality of flanges of the sleeve of FIG. 1. As shown, the second sleeve portion is in the first position and the flanges are radially collapsed.
Figure 12:
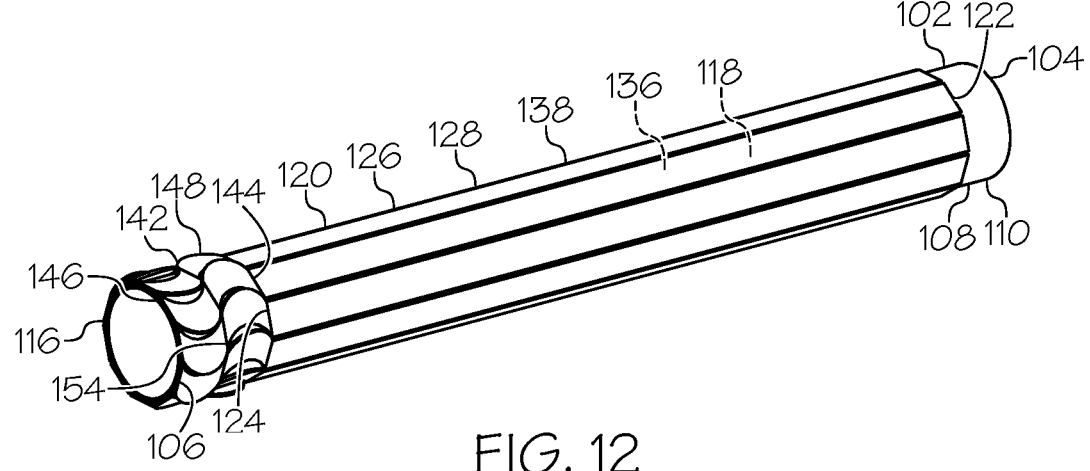
FIG. 12 is a second perspective view of the first sleeve portion, the second sleeve portion, the plurality of flanges of FIG. 11.
Figure 13:
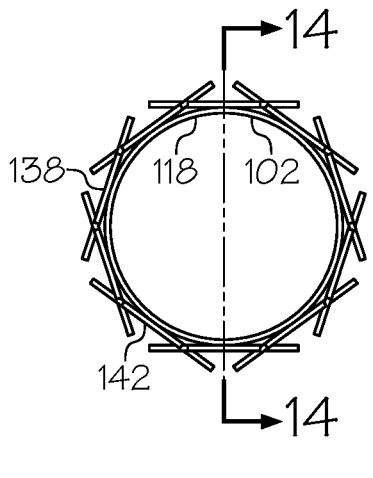
FIG. 13 is a front view of the first sleeve portion, the second sleeve portion, the plurality of flanges of FIG. 11.
Figure 14:
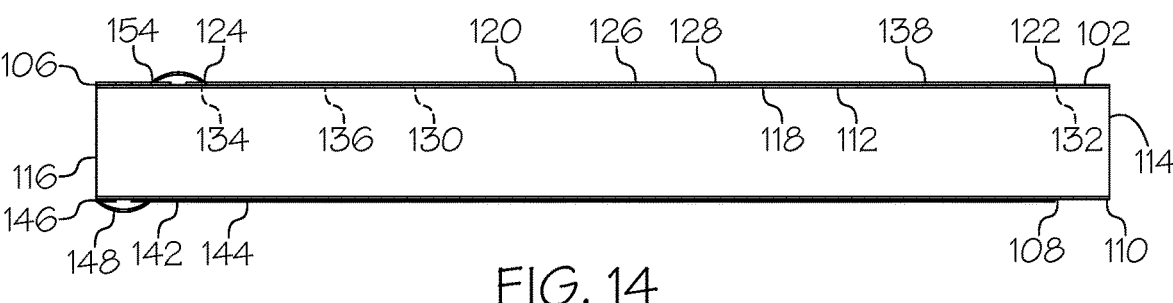
FIG. 14 is a sectional view of the first sleeve portion, the second sleeve portion, the plurality of flanges of FIG. 11, viewed along the cutting plane shown in FIG. 13.
Figure 15:
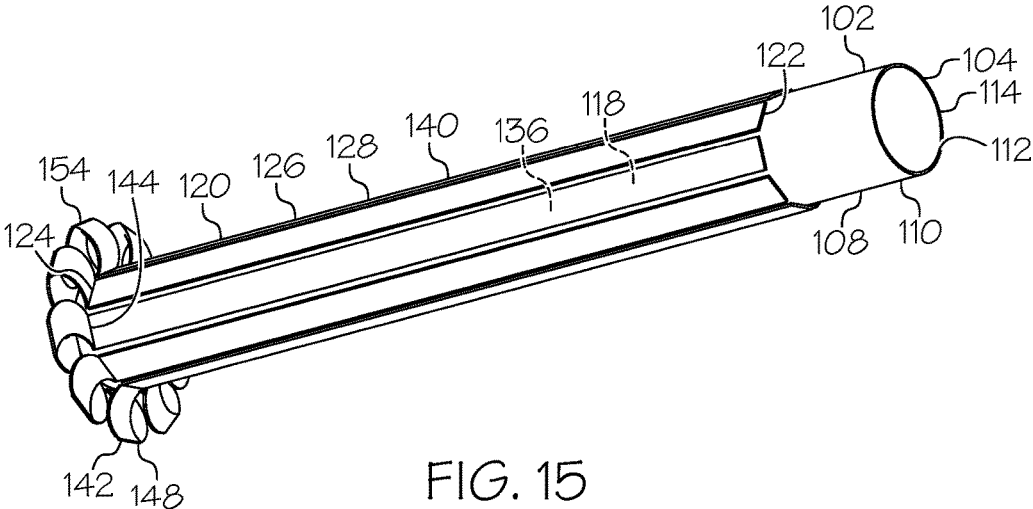
FIG. 15 is a first perspective view of the first sleeve portion, the second sleeve portion, the plurality of flanges of FIG. 11. As shown, the second sleeve portion is in the second position and the flanges are radially expanded.
Figure 16:
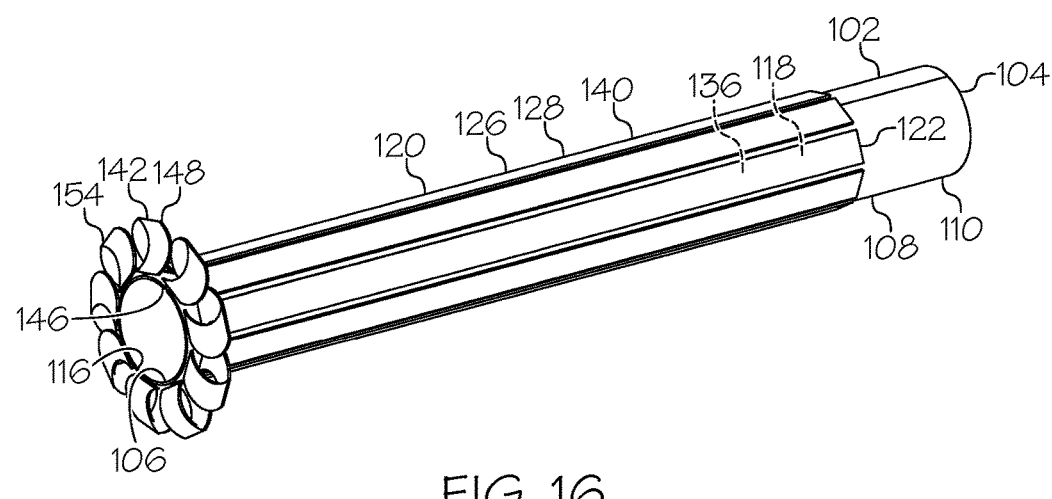
FIG. 16 is a second perspective view of the first sleeve portion, the second sleeve portion, the plurality of flanges of FIG. 15.
Figure 17:
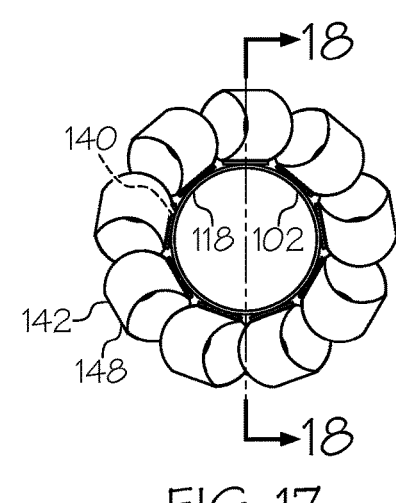
FIG. 17 is a front view of the first sleeve portion, the second sleeve portion, the plurality of flanges of FIG. 15.
Figure 18:
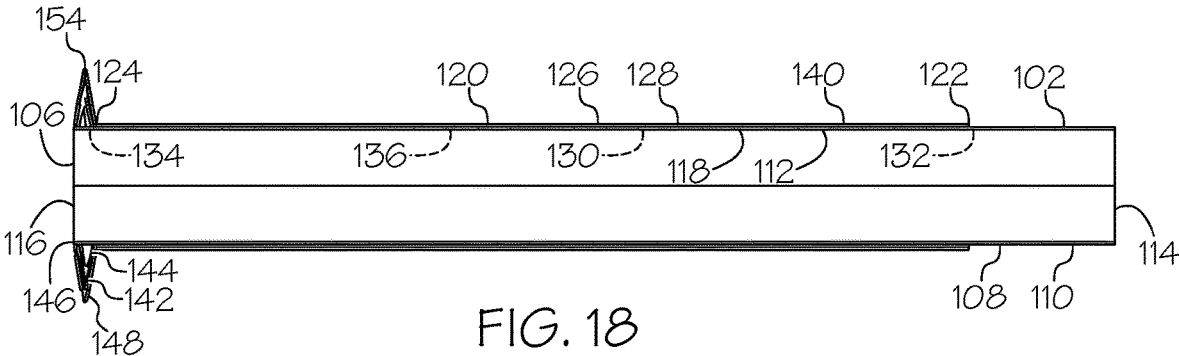
FIG. 18 is a sectional view of the first sleeve portion, the second sleeve portion, the plurality of flanges of FIG. 15, viewed along the cutting plane shown in FIG. 17.

In some embodiments, each flange 142 has a radial length 150 of 1 to 15 mm when radially expanded around the first sleeve portion 102. With reference to FIG. 7, radial length 150 means a length of the flange 142 along the flange strip 148 from where the distal end 146 of the flange 142 extends from the first sleeve portion 102 to a portion of the flange 142 that is most radially distal from the first sleeve portion 102 when the flange 142 is radially expanded. In some examples, each flange 142 has a radial length 150 of 2 to 14 mm, 3 to 13 mm, 4 to 12 mm, or 5 to 10 mm. In some examples each flange 142 has a radial length 150 of 1, 2, 3, 4, 5, 6, 7, 8, 9, 10, 11, 12, 13, 14, or 15 mm.

As noted above, moving the second sleeve portion 120 distally to the second position 140 causes the flanges 142 to fold and extend radially from the outer surface 110 of the first sleeve portion body 108. Thus, the radial length 150 of each flange 142 is approximately half of the length of each flange 142 from the proximal end 144 to the distal end 146 of the flange 142. Thus, for example, for sleeves 100 in which each flange 142 has a radial length 150 of 5 mm when radially expanded around the first sleeve portion 102, each flange 142 has a length from the proximal end 144 to the distal end 146 of the flange 142 of approximately 10 mm. Likewise, for sleeves 100 in which each flange 142 has a radial length 150 of 10 mm when radially expanded around the first sleeve portion 102, each flange 142 has a length from the proximal end 144 to the distal end 146 of the flange 142 of approximately 20 mm.

This is relevant to placement and removal of the sleeve 100 and a surgical port 500 therein into and from surgical cavities of patients. During placement, the sleeve 100 is inserted through an incision in a body wall of a patient and into a surgical cavity to at least a distance corresponding to the length of the flanges 142 from their proximal to distal ends 144, 146. This is so that the collapsed flanges 142 have passed entirely through the incision and are located entirely within the surgical cavity prior to radially expanding the flanges 142. This is to prevent tissue of the body wall from impeding radial expansion of the flanges 142. Once the sleeve 100 has been inserted at least to this extent, the second sleeve portion 120 can be moved distally from the first position 138 to the second position 140 to radially expand the flanges 142. Once the flanges 142 have been radially expanded, the first and second sleeve portions 102, 120 can be partially withdrawn together, causing the radially expanded flanges 142 to withdraw toward the incision, until the radially expanded flanges 142 contact tissue of the surgical cavity adjacent the incision and are prevented from withdrawing further, while enabling retraction of the tissues of the surgical cavity. This process can be carried out in reverse for removal of the sleeve 100 and surgical port 500 from the surgical cavity.

The sleeve 100 should have a low profile in order to not inhibit minimal surgical port depth within surgical cavities. Advantageously, the sleeve 100 allows use of surgical ports 500 at depths of 3.0 mm or less while reliably retaining the surgical ports 500 within surgical cavities.

In some embodiments each flange 142 is integral to the first and second sleeve portions 102, 120. This can be advantageous for ease of manufacturing the sleeve 100 from a single compound and/or composition and/or from a single initial piece of material.

Also in some embodiments, each flange 142 is attached to the first and second sleeve portions 102, 120. This can be advantageous for flexibility in manufacturing the flanges 142 from different compounds and/or compositions and/or pieces of material than the first and/or second sleeve portions 102, 120.

Figures 19, 20, 21:
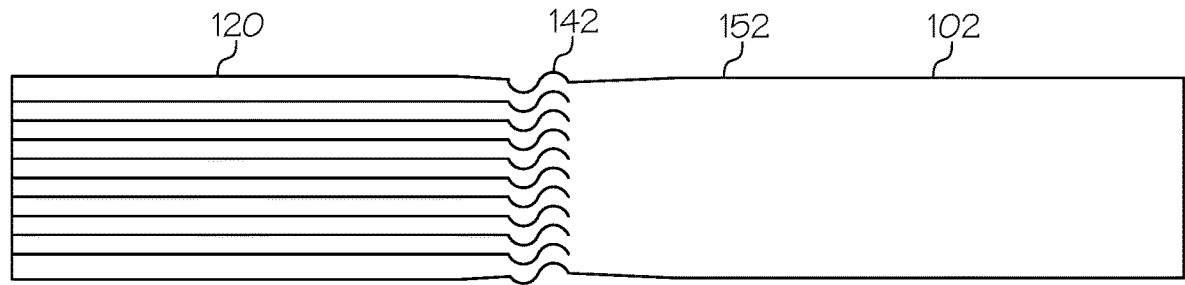
FIG. 19 shows a cutout of a thin semi-rigid plastic film having a rectangular shape with a long axis and short axis from which a first sleeve portion, a second sleeve portion, and a plurality of flanges of a first sleeve as described herein, with sigmoid-shaped cuts, can be made as described in Example 2.
FIG. 20 is a perspective view of the reversible locking mechanism of the sleeve of FIG. 1. The reversible locking mechanism as shown includes first and second clamps and first and second housings.
FIG. 21 is a top view of the reversible locking mechanism of FIG. 20.
Figure 22:
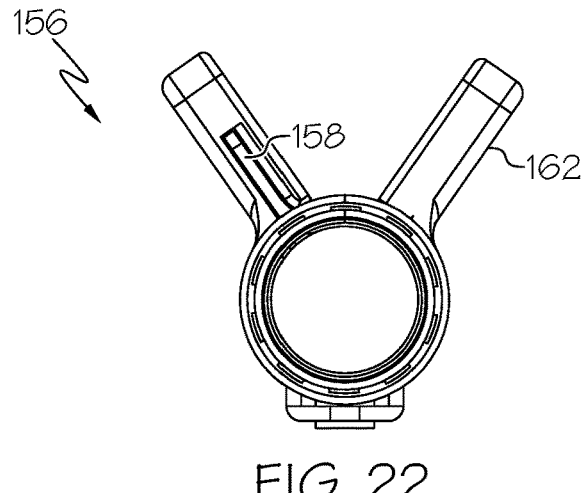
FIG. 22 is a front view of the reversible locking mechanism of FIG. 20.
Figure 23:
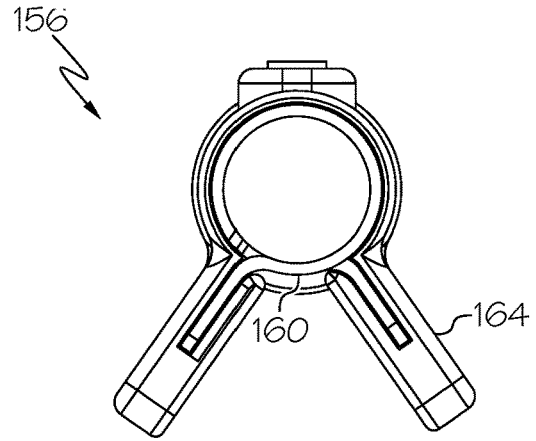
FIG. 23 is a back view of the reversible locking mechanism of FIG. 20.
Figure 24:
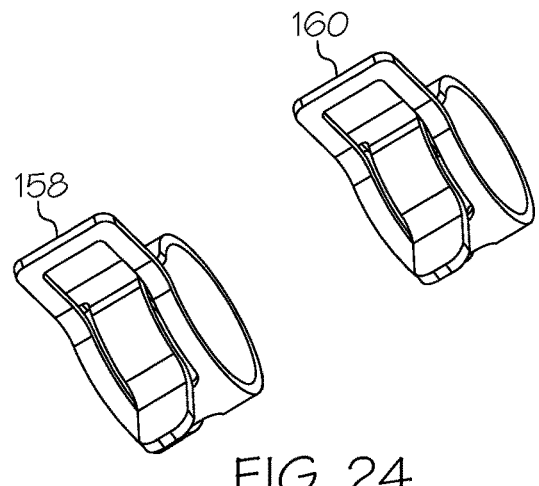
FIG. 24 is a first perspective view of the first and second clamps of the reversible locking mechanism of FIG. 20.
Figure 25:
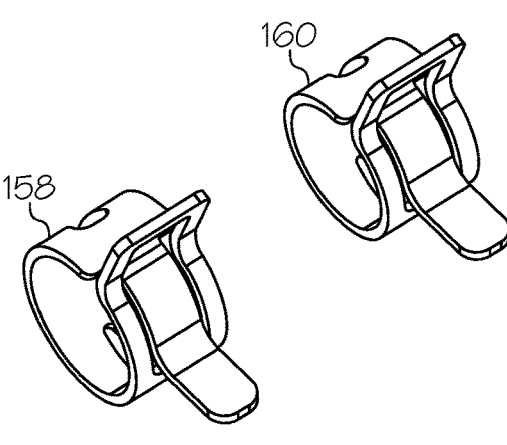
FIG. 25 is a second perspective view of the first and second clamps of FIG. 24.
Figure 26:
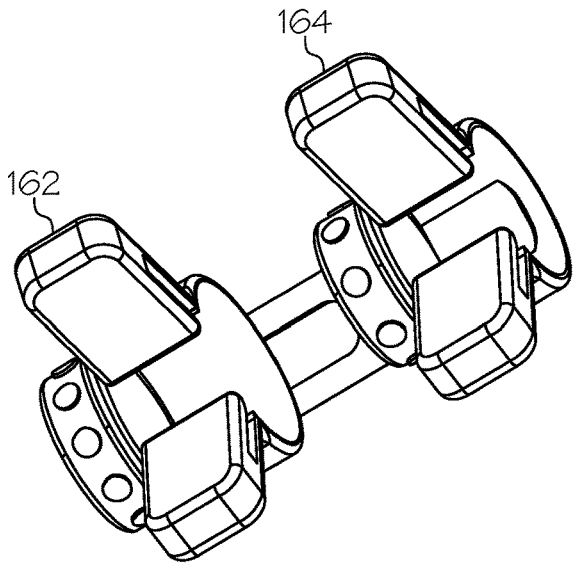
FIG. 26 is a first perspective view of the first and second housings of the reversible locking mechanism of FIG. 20.
Figure 27:
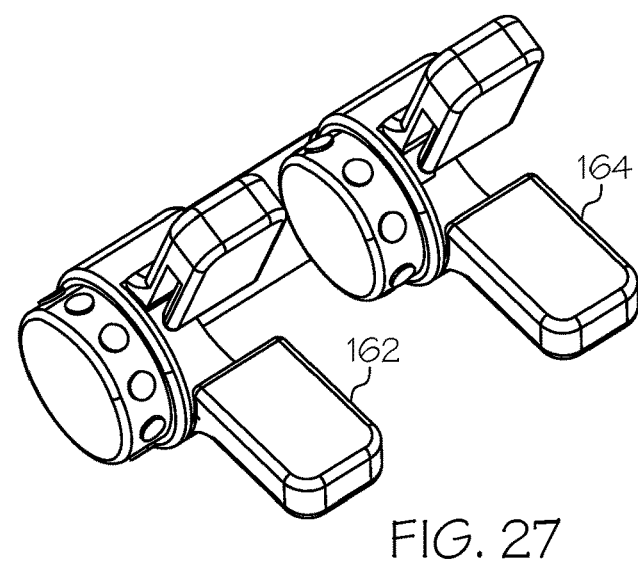
FIG. 27 is a second perspective view of the first and second housings of FIG. 26.

As shown in FIGS. 1-3, FIG. 6, FIG. 11, FIG. 12, and FIGS. 15-17, in some embodiments, each flange 142 has a sigmoidal shape. With reference to FIG. 19, this can be accomplished, for example, by preparing the first sleeve portion 102, the second sleeve portion 120, and the flanges 142 integrally from a piece of semi-rigid film 152 made, for example, from polycarbonate, and using a plotter-cutter to cut the semi-rigid film 152. The plotter-cutter can be used to cut the semi-rigid film 152 along a long axis of the semi-rigid film 152. A portion of the semi-rigid film 152 that is not cut can become the first sleeve portion 102. A portion of the semi-rigid film 152 that is cut with straight lines can become the second sleeve portion 120. A remaining portion of the semi-rigid film 152 that is cut with sigmoidal lines extending from the straight lines can become the flanges 142.

Flanges 142 having a sigmoidal shape can be advantageous for preventing tissue from occupying open spaces between flanges 142 when the flanges 142 are radially expanded, which otherwise might destabilize the flanges 142 and prevent their return to a collapsed state.

Flanges 142 having a sigmoidal shape also can be advantageous for stability of the flanges 142 when radially expanded, based on each flange 142 providing support for an adjacent flange 142.

Flanges 142 having a sigmoidal shape also can be advantageous for preventing blood from dripping over the distal opening of the first sleeve portion body 108 and instead causing blood to flow around the flanges 142 and away from the distal opening 116. With conventional surgical ports 500 placed without a sleeve 100 as disclosed herein, intraoperative bleeding in the vicinity of a camera present within the surgical port 500 can obscure the camera view. This can occur, for example, if a blood vessel is cut at the surgical cavity. The blood typically flows on the surgical port 500 and over and into its distal opening. In contrast, for a surgical port 500 placed including the sleeve 100, blood from a cut vessel contacts the flanges 142 and flows around them, instead of dripping over and through the distal opening 116 of the first sleeve portion body 108. This prevents intraoperative bleeding in the vicinity of a camera present within the surgical port 500 from obscuring the camera view.

In other embodiments, each flange 142 can have other shapes, for example, hexagonal shapes, among others.

With reference to FIGS. 11-18 and FIGS. 35-38, in some embodiments, each flange 142 has an intermediate portion 154 between the proximal and distal ends 144, 146 of the flange 142 and a width that decreases distally from the proximal end 144 of the flange 142 to the intermediate portion 154 and that increases distally from the intermediate portion 154 to the distal end 146 of the flange 142. In some of these embodiments, the intermediate portion 154 can be approximately equidistant from the proximal and distal ends 144, 146 of the flanges 142. In these embodiments, when the flanges 142 are radially expanded around the first sleeve portion 102 the flanges 142 extend approximately perpendicularly from the first sleeve portion 102. In others of these embodiments, the intermediate portion 154 can be closer to the proximal end 144 of the flange 142 than the distal end 146 of the flange 142. In these embodiments, when the flanges 142 are radially expanded around the first sleeve portion 102, the flanges 142 extend at an acute angle proximally from the first sleeve portion 102. In still others of these embodiments, the intermediate portion 154 can be closer to the distal end 146 of the flange 142 than the proximal end 144 of the flange 142. In these embodiments, when the flanges 142 are radially expanded around the first sleeve portion 102, the flanges 142 extend at an acute angle distally from the first sleeve portion 102.

Like the first and second sleeve portions 102, 120, in some embodiments the flanges 142 can be made, for example, from one or more of polyethylene terephthalate glycol, polycarbonate, or polystyrene. This can be advantageous as the resulting flanges 142 can be semi-rigid, allowing the flanges 142 to be sufficiently flexible that surgical tools can move and manipulate the flanges 142 without damaging or breaking the flanges 142. This also can be advantageous for preventing the flanges 142 from damaging tissues of the patient during placement and use. Also, as noted, these materials are biocompatible for transient contact and sterilizable.

Thus, in some embodiments the first sleeve portion 102, the second sleeve portion 120, and the plurality of flanges 142 are made from one or more of polyethylene terephthalate glycol, polycarbonate, or polystyrene.

As shown in FIGS. 1-10, the sleeve 100 also comprises a reversible locking mechanism 156 that can be reversibly actuated to prevent the second sleeve portion 120 from sliding along the first sleeve portion 102 when the second sleeve portion 120 is in the second position 140. The reversible locking mechanism 156 also can be used for preventing the sleeve 100 from unintentionally sliding along the surgical port 500. The reversible locking mechanism 156 can be locked to hold the first and second sleeve portions 102, 120 together when the second sleeve portion 120 is in the first position 138 and the flanges 142 are radially collapsed. This allows for insertion of the sleeve 100 and surgical port 500 therein into the body space of a patient, including a surgical cavity. The reversible locking mechanism 156 can then be unlocked, allowing the second sleeve portion 120 to slide along the first sleeve portion 102 to the second position 140 and the flanges 142 to become radially expanded. Once the second sleeve portion 120 is in the second position 140 and the flanges 142 are radially expanded, the reversible locking mechanism 156 can then be locked again to hold the first and second sleeve portions 102, 120 together. This maintains the flanges 142 as radially expanded as the sleeve 100 and surgical port 500 therein are translated and rotated within the surgical cavity, thus ensuring retention of the sleeve 100 and surgical port 500 within the surgical cavity. While the reversible locking mechanism 156 is locked, it also can hold the sleeve 100 and the surgical port 500 together, preventing the sleeve 100 from sliding along the surgical port 500, as discussed below.

The reversible locking mechanism 156 can be, for example, a collar, a clamp, or a ratchet mechanism, among other reversible locking mechanisms.

One example of a reversible locking mechanism 156 is a collar comprising collar flanges similar to the plurality of flanges 142 at the distal end 104 of the first sleeve portion 102 described above, disposed on the first sleeve portion 102 proximally to the second sleeve portion 120. In this configuration, the collar flanges thus may be considered proximal flanges and the flanges 142 at the distal end 106 of the first sleeve portion 102 may be considered distal flanges. In accordance with this reversible locking mechanism 156, when the proximal flanges are expanded, the second sleeve portion 120 is in the first position 138 and the distal flanges are radially collapsed. This allows insertion of the sleeve 100 and a surgical port 500 therein through an incision into a surgical cavity. Squeezing the collar causes the proximal flanges to collapse, pushing the second sleeve portion 120 from the first position 138 to the second position 140, and thus secondarily causes the distal flanges to radially expand. This allows retention of the surgical port 500 within the surgical cavity. Reversing this action returns the second sleeve portion 120 to the first position 138, allowing withdrawal of the sleeve 100 and surgical port 500 from the surgical cavity.

Regarding a reversible locking mechanism 156 that includes a clamp, the clamp can be, for example, a snap clamp, among other clamps. The snap clamp can be reversibly applied and released.

Regarding a reversible locking mechanism 156 that includes a ratchet mechanism, the ratchet mechanism can be a sliding ratchet mechanism, among other ratchet mechanisms.

As shown in FIGS. 1-10, with reference to FIGS. 20-27, in some embodiments, the reversible locking mechanism 156 can comprise first and second clamps 158, 160 and first and second housings 162, 164, and can be reversibly actuated to prevent the second sleeve portion 120 from sliding along the first sleeve portion 102 when the second sleeve portion 120 is in the second position 140 and to prevent the sleeve 100 from unintentionally sliding along the surgical port 500.

As noted above, the first sleeve portion 102 is configured for placement of a surgical port 500 through the proximal opening 114 of the first sleeve portion body 108 and into the lumen 118 of the first sleeve portion body 108 to the distal opening 116 of the first sleeve portion body 108. Also, the first sleeve portion 102 also is configured to be fixedly secured to the surgical port 500 along the inner surface 112 of the first sleeve portion body 108 by, for example, friction and/or the reversible locking mechanism 156. Regarding friction, the first sleeve portion 102 can be fixedly secured to the surgical port 500 along the inner surface 112 of the first sleeve portion body 108 based, for example, on the first sleeve portion 102 and the surgical port 500 having a close frictional complementary fit. Regarding the reversible locking mechanism 156, alternatively or additionally the first sleeve portion 102 can be fixedly secured to the surgical port 500 along the inner surface 112 of the first sleeve portion body 108 based, for example, on the reversible locking mechanism 156 compressing the first sleeve portion 102 about the surgical port 500 when locked.

Figure 28:
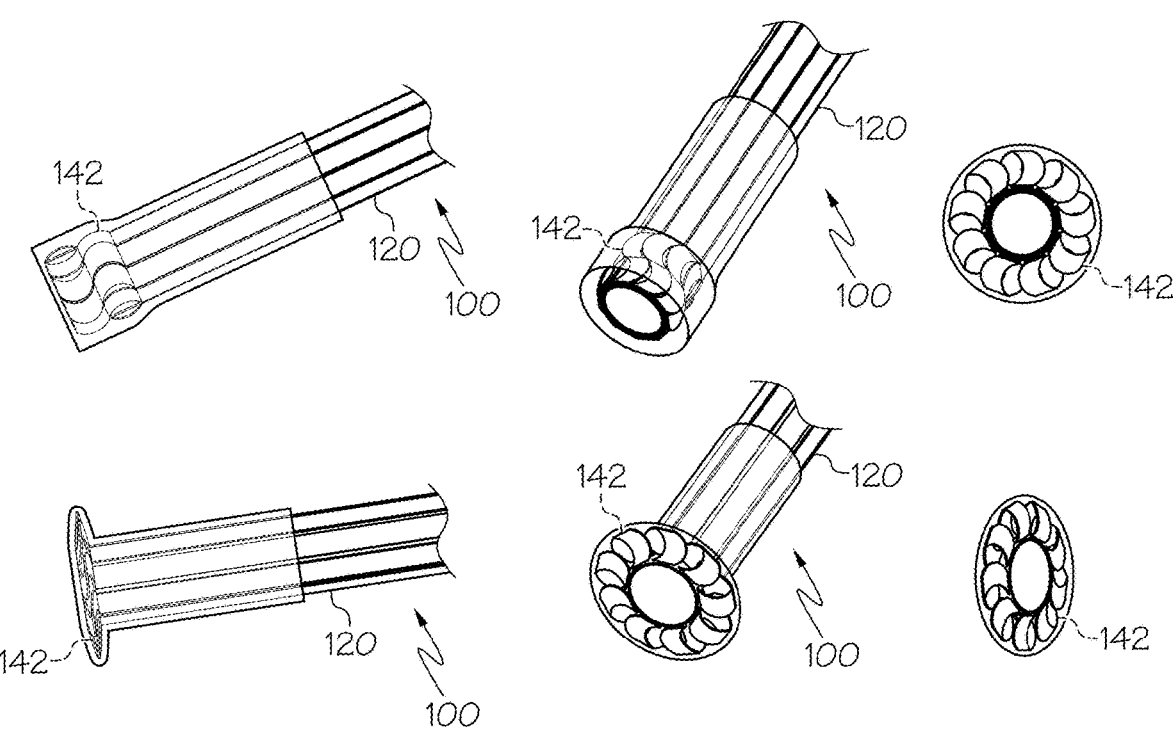
FIG. 28 shows images of an exemplary first sleeve as described herein further comprising a flexible film covering a second sleeve portion and a plurality of flanges of the sleeve.

As shown in FIG. 28, in some embodiments, the sleeve 100 further comprises a flexible film covering the second sleeve portion 120 and the plurality of flanges 142, the flexible film being adhered to the first sleeve portion 102 at the distal end 106 of the first sleeve portion 102 and to the second sleeve portion 120 along the outer surface 128 of the second sleeve portion body 126, and the flexible film not being adhered to the plurality of flanges 142. This can be advantageous for protecting tissue in a surgical cavity from being injured by edges of the flanges 142 based on the flexible film covering the first sleeve portion 102, the second sleeve portion 120, and the flanges 142, without impeding radial expansion and collapse of the flanges 142. The flexible film can be made, for example, from silicone or polyurethane, among other flexible materials.

In some embodiments, the first sleeve portion 102, the second sleeve portion 120, and the flanges 142 are provided free of sharp edges. This also can be advantageous for protecting tissue of a patient from being injured.

The sleeve 100 can be provided as a single use sterile device.

Figure 29:
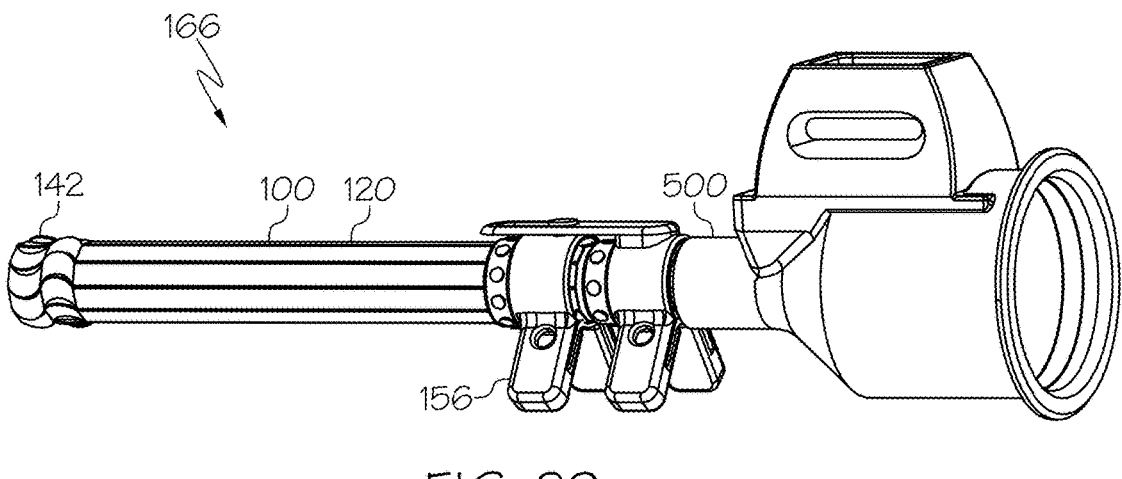
FIG. 29 is a first perspective view of an exemplary first system for retention of a surgical port as described herein comprising the sleeve of FIG. 1 and a surgical port.
Figure 30:
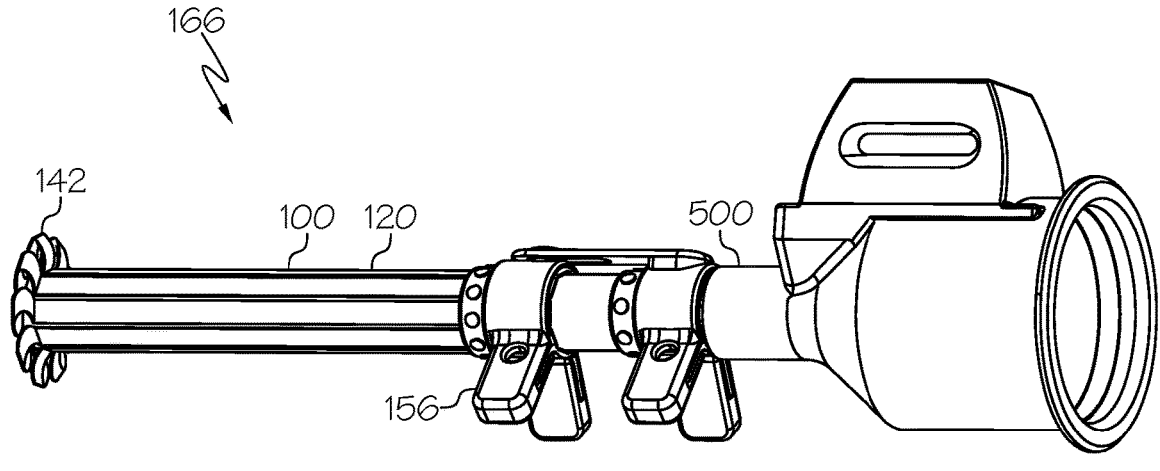
FIG. 30 is a second perspective view of the system of FIG. 29.
Figure 31:
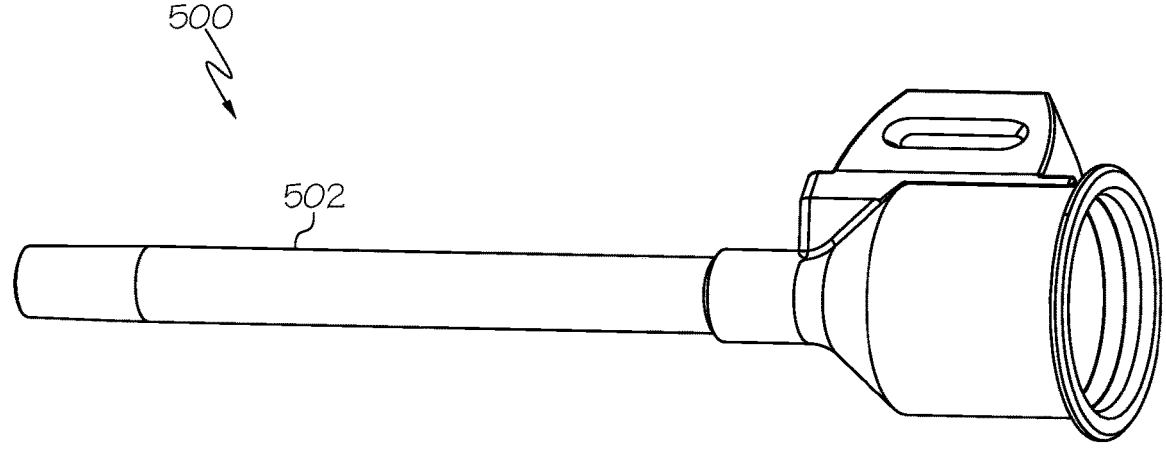
FIG. 31 is a perspective view of the surgical port of FIG. 29.
Figure 32:
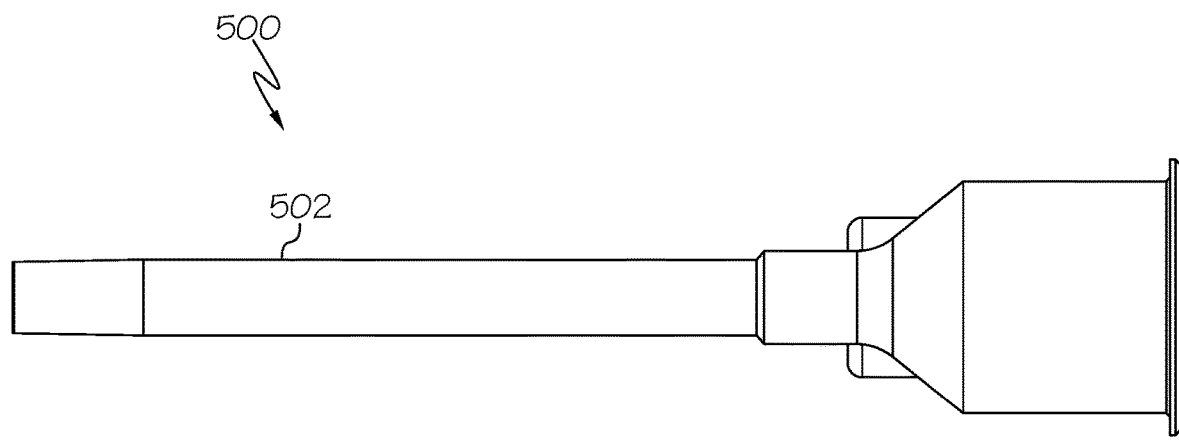
FIG. 32 is a side view of the surgical port of FIG. 31.
Figure 33:
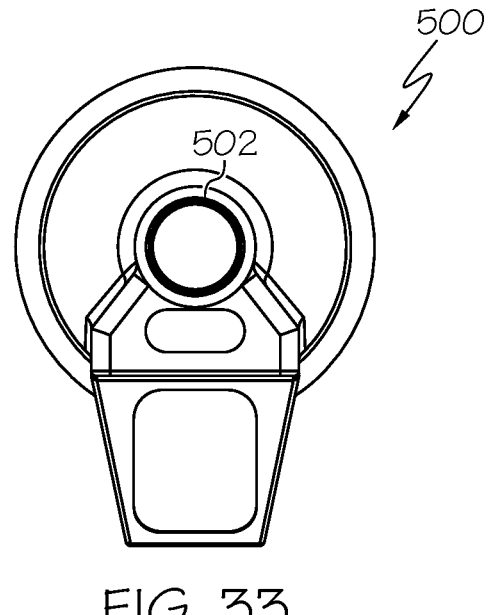
FIG. 33 is a front view of the surgical port of FIG. 31.
Figure 34:
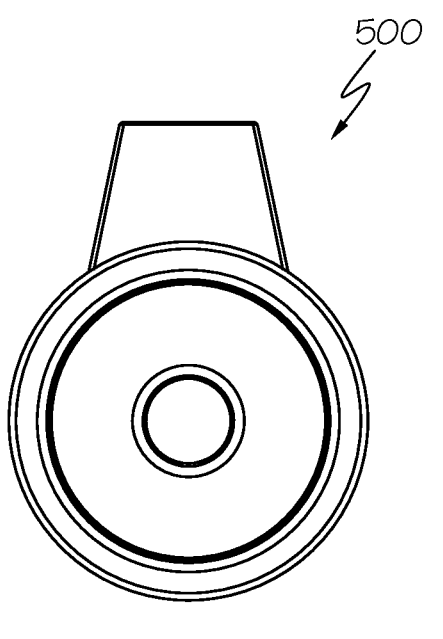
FIG. 34 is a back view of the surgical port of FIG. 31.

As shown in FIG. 29 and FIG. 30, a first system 166 for retention of a surgical port 500 also is provided. The system 166 comprises the first sleeve 100 as described above. With reference to FIGS. 31-34, the system 166 also comprises a surgical port 500. The first sleeve portion 102 of the sleeve 100 is fixedly secured to the surgical port 500 along the inner surface 112 of the first sleeve portion body 108.

A method of use of the first sleeve 100 in performing a surgery on a patient in need thereof also is provided. The method comprises steps of: (1) securing the first sleeve 100 to a surgical port 500 fixedly along the inner surface 112 of the first sleeve portion body 108; (2) inserting the surgical port 500 and the first sleeve 100 through an incision in a body wall of the patient such that the flanges 142 of the first sleeve 100 extend into a surgical cavity of the patient, wherein during the inserting the second sleeve portion 120 is in the first position 138 and the flanges 142 are radially collapsed along the first sleeve portion 102; (3) sliding the second sleeve portion 120 from the first position 138 to the second position 140, thereby radially expanding the flanges 142 around the first sleeve portion 102; (4) actuating the reversible locking mechanism 156 to prevent the second sleeve portion 120 from sliding along the first sleeve portion 102; and (5) inserting one or more surgical instruments through the surgical port 500 into the surgical cavity of the patient.

In some embodiments, the method further comprises steps of: (6) withdrawing the one or more surgical instruments from the surgical cavity of the patient through the surgical port 500; (7) releasing the reversible locking mechanism 156 to allow the second sleeve portion 120 to slide along the first sleeve portion 102; (8) sliding the second sleeve portion 120 from the second position 140 to the first position 138, thereby radially collapsing the flanges 142 along the first sleeve portion 102; and (9) withdrawing the surgical port 500 and the sleeve 100 from the surgical cavity through the incision in the body wall.

As shown in FIGS. 41-44, a second sleeve 200 for retention of a surgical port 500 also is provided. The second sleeve 200 varies from the first sleeve 100 with respect to some of its structures and configurations, as described below, but is similarly useful for maintaining a surgical port 500, such as a robotic surgical port, within a surgical cavity, for preventing the surgical port 500 from retracting into the subcutaneous space, and for maintaining optimal working space within the surgical cavity.

The sleeve 200 comprises a first sleeve portion 202 comprising a proximal end 204, a distal end 206, and a first sleeve portion body 208 extending therebetween. The first sleeve portion body 208 has an outer surface 210, an inner surface 212, a proximal opening 214, a distal opening 216, and a lumen 218 extending between the proximal and distal openings 214, 216 of the first sleeve portion body 208.

The first sleeve portion 202 can have proportions including an axial length substantially less than its diameter, like a collar, among other proportions.

The first sleeve portion 202 can be made, for example, from one or more of polyethylene terephthalate glycol, polycarbonate, or polystyrene, as described above, and this can be advantageous as described above.

The sleeve 200 also comprises a second sleeve portion 220 comprising a proximal end 202, a distal end 204, and a second sleeve portion body 226 extending therebetween. The second sleeve portion body 226 has an outer surface 228, an inner surface 230, a proximal opening 232, a distal opening 234, and a lumen 236 extending between the proximal and distal openings 232, 234 of the second sleeve portion body 226. The second sleeve portion 220 is disposed proximally to the first sleeve portion 202 and is reversibly translatable distally from a first position to a second position toward the first sleeve portion 202. For reference, FIGS. 41-44 show the second sleeve portion 220 disposed proximally to the first sleeve portion 202 in the first position. The second sleeve portion 220 in the second position is not shown, but is described below.

The second sleeve portion 220 can have proportions including an axial length substantially greater than its diameter, like a tube, among other proportions.

The second sleeve portion 220 can be made, for example, from one or more of polyethylene terephthalate glycol, polycarbonate, or polystyrene, as described above, and this can be advantageous as described above.

The sleeve 200 is configured for placement of a surgical port 500 through the lumen 236 of the second sleeve portion body 220 and into the lumen 218 of the first sleeve portion body 208 to the distal opening 216 of the first sleeve portion body 208, for the sleeve 200 to be fixedly secured to the surgical port 500 along the inner surface 212 of the first sleeve portion body 208, and for the inner surface 230 of the second sleeve portion body 226 to be in slidable contact with the surgical port 500. This configuration can be accomplished, for example, based on the first sleeve portion 202 and the second sleeve portion 220 having a complementary fit with the surgical port 500.

The sleeve 200 also comprises a plurality of flanges 242 disposed in a radial sequence between the first sleeve portion 202 and the second sleeve portion 220. Each flange 242 has a proximal end 244, a distal end 246, and a flange strip 248 extending therebetween. The proximal end 244 of each flange 242 extends from the distal end 224 of the second sleeve portion 220 in the radial sequence. The distal end 246 of each flange 242 extends from the proximal end 204 of the first sleeve portion 202 in the radial sequence. The flanges 242 are radially collapsed when the second sleeve portion 220 is in the first position and are radially expanded when the second sleeve portion 220 is in the second position.

In some embodiments, the plurality of flanges 242 consists of 5 to 25 flanges. For example, in some embodiments the plurality of flanges 242 consists of 6 to 20 flanges, 7 to 17 flanges, or 8 to 15 flanges, among other ranges. Also in some embodiments the plurality of flanges 242 consists of 5, 6, 7, 8, 9, 10, 11, 12, 13, 14, 15, 16, 17, 18, 19, 20, 21, 22, 23, 24, or 25 flanges. Making the sleeve 200 with a relatively low number of flanges 242, e.g., 5 to 8 flanges, can be advantageous for promoting rigidity of the flanges 242. Making the sleeve 200 with a relatively high number of flanges 242, e.g., 15 to 25 flanges, can be advantageous for providing the flanges 242 with a more rounded shape when folded, reducing the sharpness of their edges and reducing open spaces between adjacent flanges 242.

In some embodiments, each flange 242 has a radial length of 1 to 15 mm when radially expanded. In some examples, each flange 242 has a radial length of 2 to 14 mm, 3 to 13 mm, 4 to 12 mm, or 5 to 10 mm. In some examples each flange 242 has a radial length of 1, 2, 3, 4, 5, 6, 7, 8, 9, 10, 11, 12, 13, 14, or 15 mm.

Translating the second sleeve portion 220 distally to the second position causes the flanges 242 to fold and extend radially similarly as described above. Again, the radial length of each flange 242 is approximately half of the length of each flange 242 from the proximal end 244 to the distal end 246 of the flange 242. Thus, for example, for sleeves 200 in which each flange 242 has a radial length of 5 mm when radially expanded, each flange 242 has a length from the proximal end 244 to the distal end 246 of the flange 242 of approximately 10 mm. Likewise, for sleeves 200 in which each flange 242 has a radial length of 10 mm when radially expanded, each flange 242 has a length from the proximal end 244 to the distal end 246 of the flange 242 of approximately 20 mm. This is relevant for reasons as discussed above.

In some embodiments each flange 242 is integral to the first and second sleeve portions 202, 220. This can be advantageous as discussed above.

Also in some embodiments, each flange 242 is attached to the first and second sleeve portions 202, 220. This can be advantageous also as discussed above.

In some embodiments, each flange 242 has a sigmoidal shape. This can be accomplished, for example, by preparing the first sleeve portion 202, the second sleeve portion 220, and the flanges 242 integrally from a piece of semi-rigid film made, for example, from polycarbonate, and using a plotter-cutter to cut the film, as discussed above. Flanges 242 having a sigmoidal shape can be advantageous as discussed above.

In other embodiments, each flange 242 can have other shapes, for example hexagonal shapes, among others.

In some embodiments, each flange 242 has an intermediate portion 254 between the proximal and distal ends 244, 246 of the flange 242 and a width that decreases distally from the proximal end 244 of the flange 242 to the intermediate portion 254 and that increases distally from the intermediate portion 254 to the distal end 246 of the flange 242, as discussed above.

Like the first and second sleeve portions 202, 220, in some embodiments the flanges 242 can be made, for example, from one or more of polyethylene terephthalate glycol, polycarbonate, or polystyrene. This can be advantageous as discussed above.

Thus, in some embodiments the first sleeve portion 202, the second sleeve portion 220, and the plurality of flanges 242 are made from one or more of polyethylene terephthalate glycol, polycarbonate, or polystyrene.

The sleeve 200 also comprises a reversible locking mechanism that can be reversibly actuated to prevent the second sleeve portion 220 from translating away from the first sleeve portion 202 when the second sleeve portion 220 is in the second position. The reversible locking mechanism also can be used for preventing the sleeve 200 from unintentionally sliding along the surgical port 500. The reversible locking mechanism is not shown in combination with the first sleeve portion 202, the second sleeve portion 220, and the flanges 242, but can be, for example, a collar, a clamp, or a ratchet mechanism, among other reversible locking mechanisms, as described above.

In some embodiments, the first sleeve portion 202, the second sleeve portion 220, and the flanges 242 are provided free of sharp edges. This also can be advantageous for protecting tissue of a patient from being injured.

The sleeve 200 can be provided as a single use sterile device.

A second system for retention of a surgical port 500 also is provided. The system comprises the second sleeve 200 as described above. The system also comprises a surgical port 500. The first sleeve portion 202 is fixedly secured to the surgical port 500 along the inner surface 212 of the first sleeve portion body 208.

A method of use of the second sleeve 200 in performing a surgery on a patient in need thereof also is provided. The method comprises steps of: (1) securing the second sleeve 200 to a surgical port 500 fixedly along the inner surface 212 of the first sleeve portion body 208; (2) inserting the surgical port 500 and the second sleeve 200 through an incision in a body wall of the patient such that the flanges 242 of the second sleeve 200 extend into a surgical cavity of the patient, wherein during the inserting the second sleeve portion 220 is in the first position and the flanges 242 are radially collapsed; (3) translating the second sleeve portion 220 from the first position to the second position, thereby radially expanding the flanges 242; (4) actuating the reversible locking mechanism to prevent the second sleeve portion 220 from translating away from the first sleeve portion 202; and (5) inserting one or more surgical instruments through the surgical port 500 into the surgical cavity of the patient.

In some embodiments, the method further comprises steps of: (6) withdrawing the one or more surgical instruments from the surgical cavity of the patient through the surgical port 500; (7) releasing the reversible locking mechanism to allow the second sleeve portion 220 to translate away from the first sleeve portion 202; (8) translating the second sleeve portion 220 from the second position to the first position, thereby radially collapsing the flanges 242; and (9) withdrawing the surgical port 500 and the second sleeve 200 from the surgical cavity through the incision in the body wall.

Figure 45:
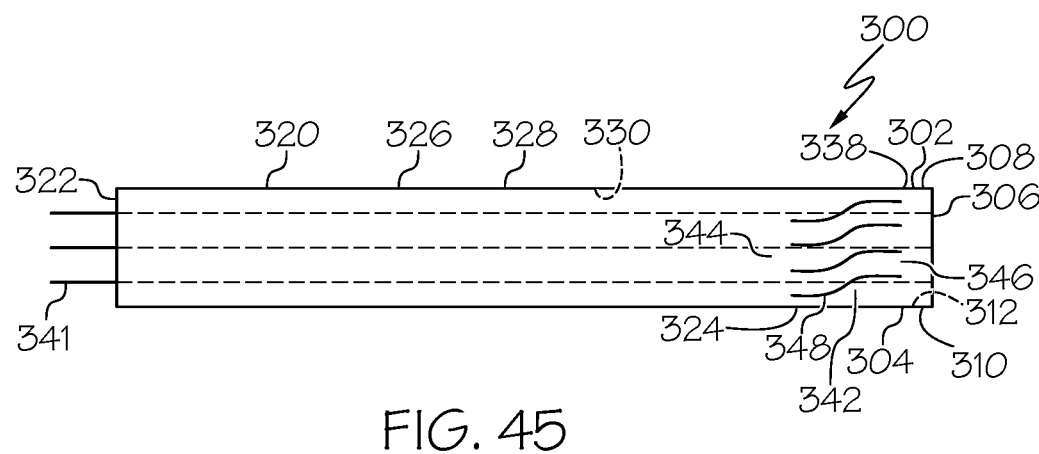
FIG. 45 is a schematic view of a first sleeve portion, a second sleeve portion, and a plurality of flanges of the third sleeve as described herein. Like the first sleeve, the third sleeve also comprises a reversible locking mechanism, which is not shown in FIG. 44, but which can be like the reversible locking mechanism shown in FIGS. 20-23. As shown, the third sleeve also comprises retraction cables attached to the first sleeve portion at the distal end of the first sleeve portion for translating the first sleeve portion from the distal position to the proximal position. As shown, the first sleeve portion is in the distal position and the flanges are radially collapsed.
Figure 46:
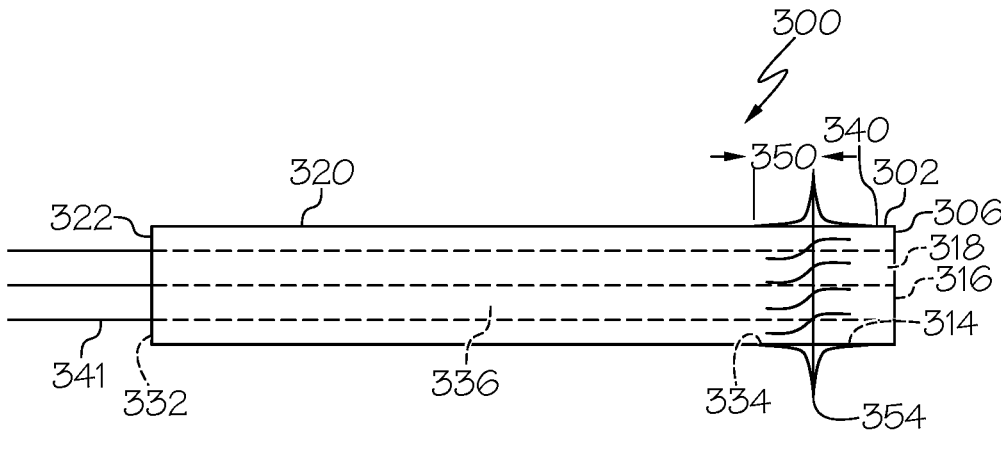
FIG. 46 is a schematic view of the first sleeve portion, the second sleeve portion, the plurality of flanges, and the retraction cables of FIG. 45. As shown, the first sleeve portion is in the proximal position and the flanges are radially expanded.
Figure 47:
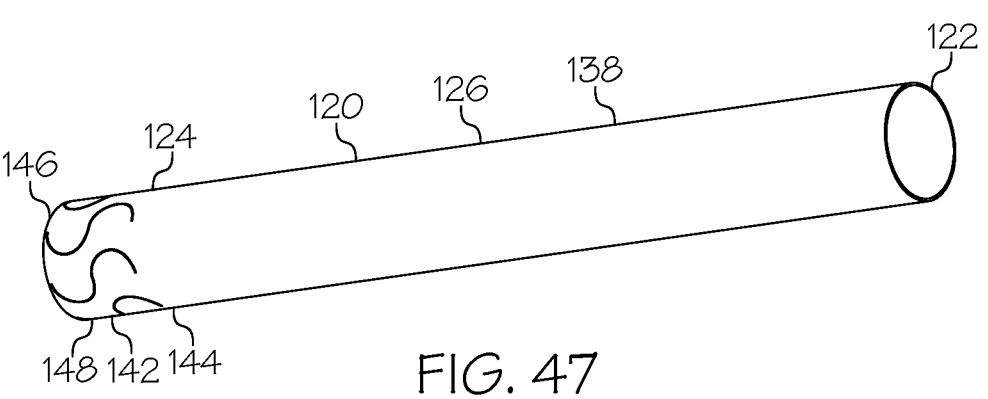
FIG. 47 is a perspective view of a first sleeve portion, a second sleeve portion, a plurality of flanges of another exemplary first sleeve for retention of a surgical port as described herein. As shown, the second sleeve portion is in the first position and the flanges are radially collapsed. The first sleeve also comprises a reversible locking mechanism, which is not shown in FIG. 47, but which can be like the reversible locking mechanism shown in FIGS. 20-23.
Figure 48:
FIG. 48 is a side view of the first sleeve portion, the second sleeve portion, the plurality of flanges of FIG. 47.
Figure 49:
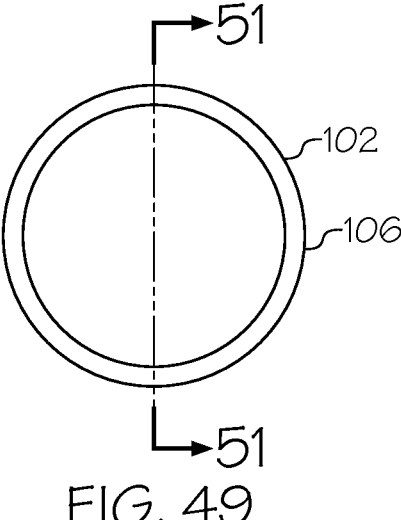
FIG. 49 is a front view of the first sleeve portion, the second sleeve portion, the plurality of flanges of FIG. 47.
Figure 50:
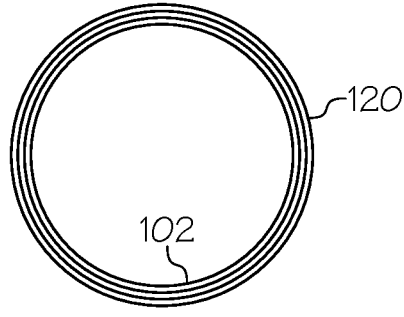
FIG. 50 is a back view of the first sleeve portion, the second sleeve portion, the plurality of flanges of FIG. 47.
Figure 51:
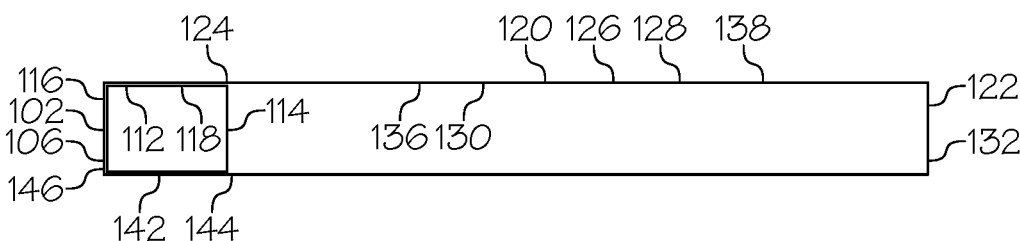
FIG. 51 is a section view of the first sleeve portion, the second sleeve portion, the plurality of flanges of FIG. 47, viewed along the cutting plane shown in FIG. 49.
Figure 52:
FIG. 52 shows a still image of a first sleeve as described herein, also referred to as a foldable sleeve, with unexpanded sigmoid-shaped cuts and a robotic port therein within the confines of a live porcine model as discussed in Example 3. As shown, the sleeve and robotic port are positioned within a surgical cavity. The flanges of the sleeve were made from a semi-rigid material. As shown, the flanges are radially collapsed.
Figure 53:
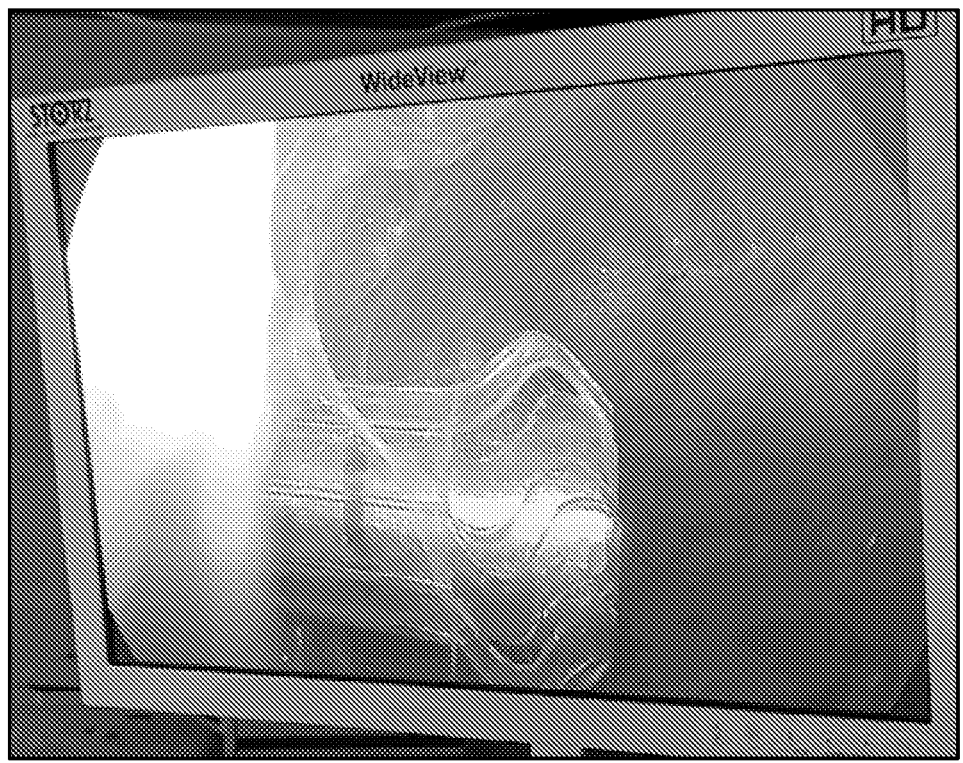
FIG. 53 shows a still image of the foldable sleeve and robotic port of FIG. 52 positioned in the surgical cavity. As shown, the flanges are partially radially expanded.
Figure 54:
FIG. 54 shows a still image of the foldable sleeve and robotic port of FIG. 52 positioned in the surgical cavity. As shown, the flanges are fully radially expanded.
Figure 55:
FIG. 55 shows a still image of the foldable sleeve and robotic port of FIG. 52 positioned in the surgical cavity. As shown, the flanges are fully radially expanded and the sleeve is being used to retain the sleeve and robotic port during retraction of tissue of the surgical cavity.
Figure 56:
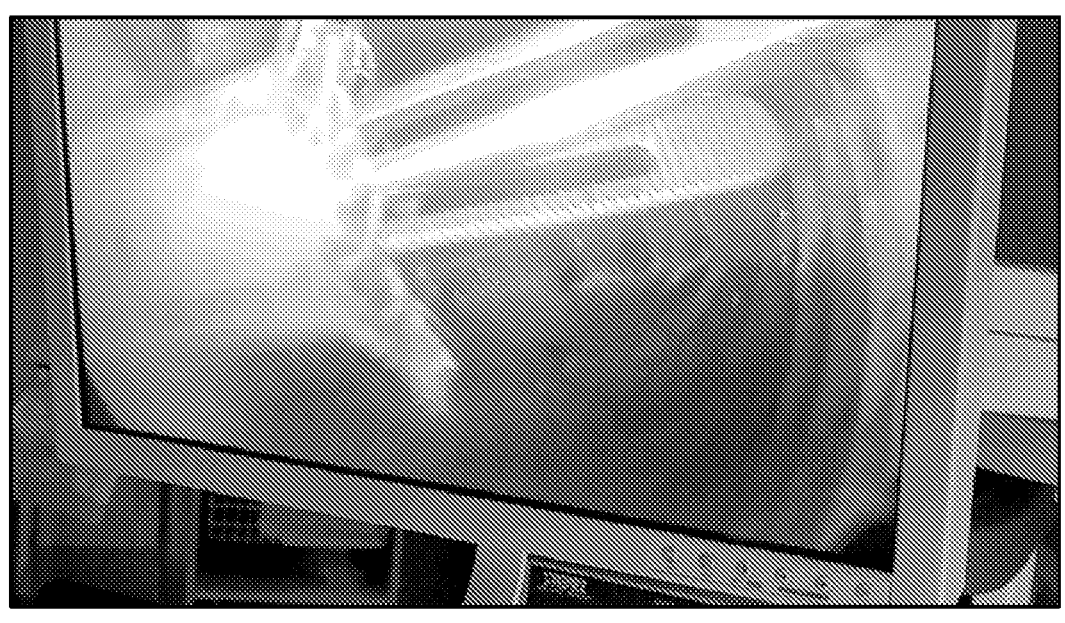
FIG. 56 shows a still image of the foldable sleeve and robotic port of FIG. 52 positioned in a surgical cavity. A surgical instrument with jaws is extending distally from the port. The sleeve and port are inserted within the surgical cavity to a depth recommended for conventional use of the port, i.e., when the port would be used without a sleeve for retention as disclosed herein. As can be seen, when the sleeve and port are inserted to this depth, there is not adequate space remaining in the surgical cavity to fully open the jaws of the surgical instrument. This illustrates a drawback associated with conventional use of a port, i.e., without the sleeve for retention.
Figure 57:
FIG. 57 shows a still image of the surgical instrument of FIG. 56 in the surgical cavity. The flanges of the foldable sleeve have been fully radially expanded and the sleeve and robotic port have been withdrawn out of the view to a sufficient extent for the flanges to retract tissue of the surgical cavity while still retaining the robotic port within the surgical cavity. As can be seen, there is now adequate space remaining in the surgical cavity to fully open the jaws of the surgical instrument. This illustrates an advantage associated with use of the sleeve as disclosed herein.
Figure 58:
FIGS. 58-61 show still images of the foldable sleeve and robotic port of FIG. 52 positioned in the surgical cavity, in which a drop of blood contacts flanges of the sleeve (FIG. 58) and then flows around the flanges (FIGS. 59-61) instead of flowing into the robotic port. This illustrates another advantage associated with use of the sleeve as disclosed herein.
Figure 59:
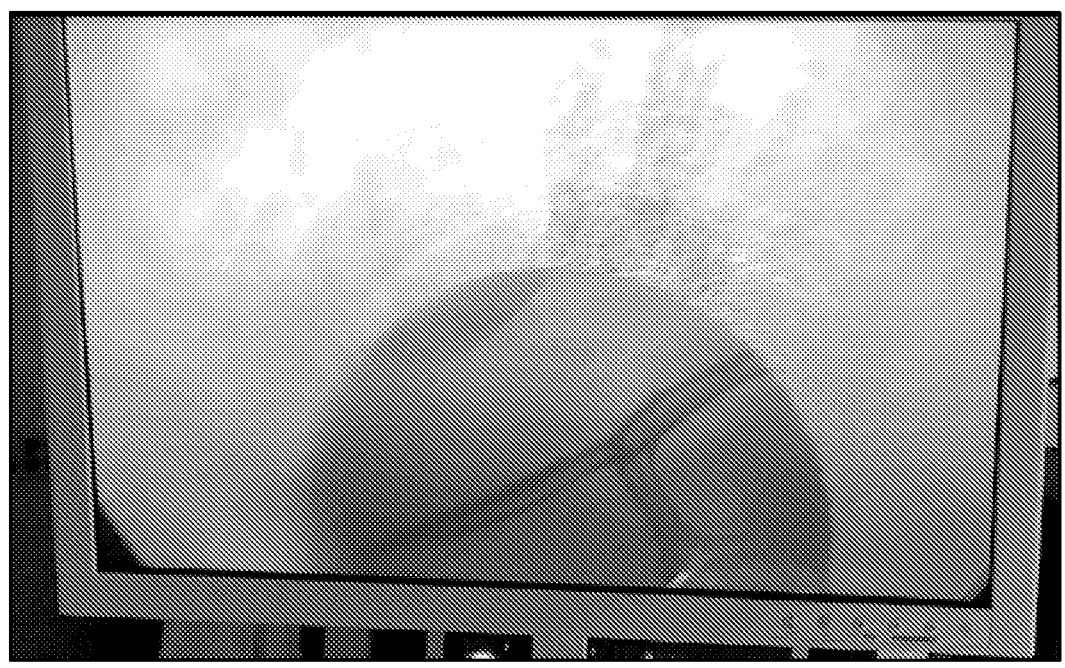
Figure 60:
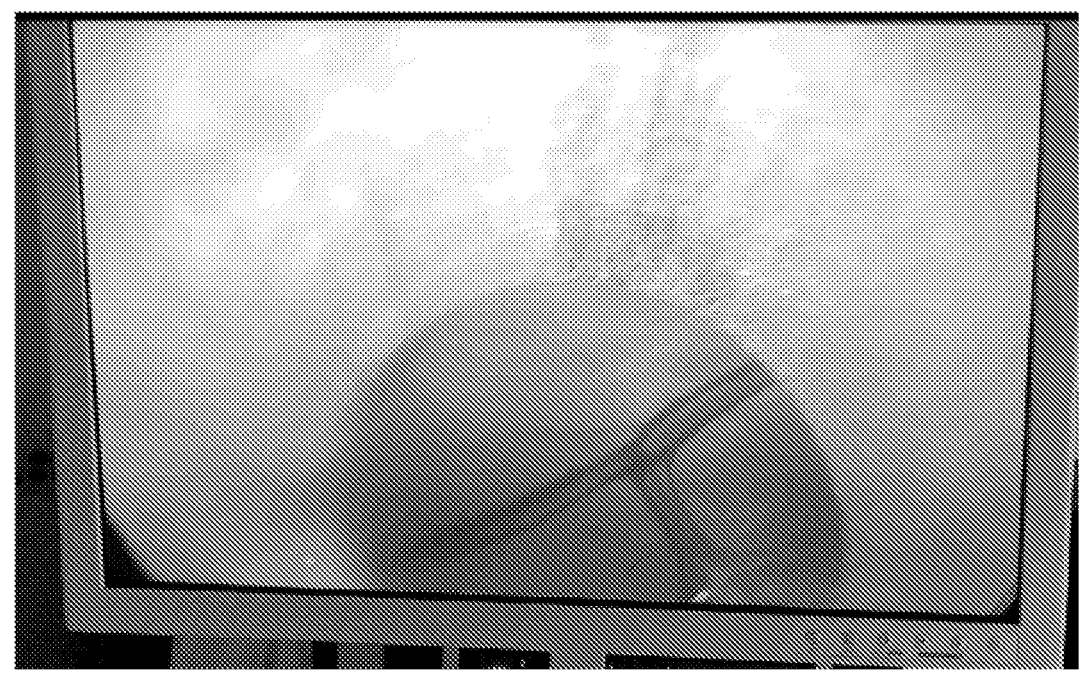
Figure 61:
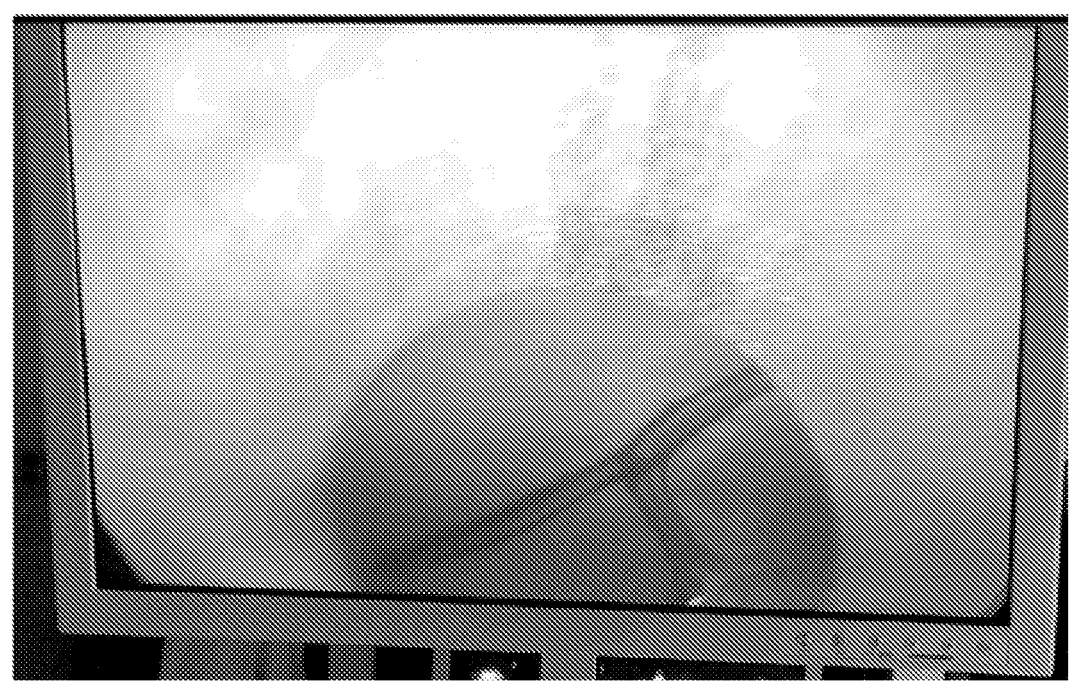
Figure 62:
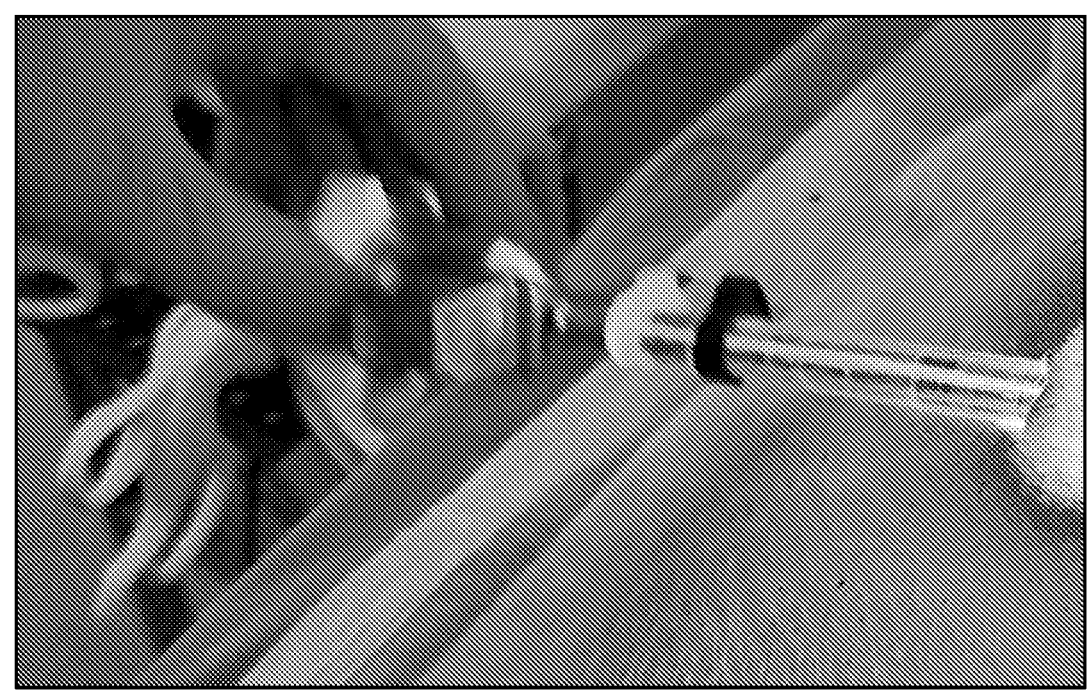
FIG. 62 shows the foldable sleeve and robotic port of FIG. 52 from outside of the porcine model. With direct external traction the port was still retained within the body cavity with a force rating of 10 Nm.

As shown in FIG. 45 and FIG. 46, a third sleeve 300 for retention of a surgical port 500 also is provided. The third sleeve 300 varies from the first sleeve 100 and the second sleeve 200 with respect to some of its structures and configurations, but is similarly useful for maintaining a surgical port 500, such as a robotic surgical port, within a surgical cavity, for preventing the surgical port 500 from retracting into the subcutaneous space, and for maintaining optimal working space within the surgical cavity.

The sleeve 300 comprises a first sleeve portion 302 comprising a proximal end 304, a distal end 306, and a first sleeve portion body 308 extending therebetween. The first sleeve portion body 308 has an outer surface 310, an inner surface 312, a proximal opening 314, a distal opening 316, and a lumen 318 extending between the proximal and distal openings 314, 316 of the first sleeve portion body 308.

The first sleeve portion 302 can have proportions including an axial length substantially less than its diameter, like a collar, among other proportions.

The first sleeve portion 302 can be made, for example, from one or more of polyethylene terephthalate glycol, polycarbonate, or polystyrene, as described above, and this can be advantageous as described above.

The sleeve 300 also comprises a second sleeve portion 320 comprising a proximal end 322, a distal end 324, and a second sleeve portion body 326 extending therebetween. The second sleeve portion body 326 has an outer surface 328, an inner surface 330, a proximal opening 332, a distal opening 334, and a lumen 336 extending between the proximal and distal openings 332, 334 of the second sleeve portion body 326.

The second sleeve portion 320 can have proportions including an axial length substantially greater than its diameter, like a tube, among other proportions.

The second sleeve portion 320 is disposed proximally to the first sleeve portion 302.

The first sleeve portion 302 is reversibly translatable proximally from a distal position 338 to a proximal position 340 toward the second sleeve portion 320.

In some embodiments, the sleeve 300 comprises one or more retraction cables 341 attached to the first sleeve portion 302 at the distal end 306 of the first sleeve portion 302 for translating the first sleeve portion 302 from the distal position 338 to the proximal position 340.

The second sleeve portion 320 is configured for placement of a surgical port 500 into the lumen 336 of the second sleeve portion body 326 and to be fixedly secured to the surgical port 500 along the inner surface 330 of the second sleeve portion body 326. This configuration can be accomplished, for example, based on the second sleeve portion 320 and the surgical port 500 having a complementary fit.

The second sleeve portion 320 can be made, for example, from one or more of polyethylene terephthalate glycol, polycarbonate, or polystyrene, as described above, and this can be advantageous as described above.

The sleeve 300 also comprises a plurality of flanges 342 disposed in a radial sequence between the first sleeve portion 302 and the second sleeve portion 320. Each flange 342 has a proximal end 344, a distal end 346, and a flange strip 348 extending therebetween. The proximal end 344 of each flange 342 extends from the distal end 324 of the second sleeve portion 320 in the radial sequence. The distal end 346 of each flange 342 extends from the proximal end 304 of the first sleeve portion 302 in the radial sequence. The flanges 342 are radially collapsed when the first sleeve portion 302 is in the distal position 340 and are radially expanded when the first sleeve portion 302 is in the proximal position 340.

In some embodiments, the plurality of flanges 342 consists of 5 to 25 flanges. For example, in some embodiments the plurality of flanges 342 consists of 6 to 20 flanges, 7 to 17 flanges, or 8 to 15 flanges, among other ranges. Also in some embodiments the plurality of flanges 342 consists of 5, 6, 7, 8, 9, 10, 11, 12, 13, 14, 15, 16, 17, 18, 19, 20, 21, 22, 23, 24, or 25 flanges. Making the sleeve 300 with a relatively low number of flanges 342, e.g., 5 to 8 flanges, can be advantageous for promoting rigidity of the flanges 342. Making the sleeve 300 with a relatively high number of flanges 342, e.g., 15 to 25 flanges, can be advantageous for providing the flanges 342 with a more rounded shape when folded, reducing the sharpness of their edges and reducing open spaces between adjacent flanges 342.

In some embodiments, each flange 342 has a radial length of 1 to 15 mm when radially expanded. In some examples, each flange 342 has a radial length of 2 to 14 mm, 3 to 13 mm, 4 to 12 mm, or 5 to 10 mm. In some examples each flange 342 has a radial length of 1, 2, 3, 4, 5, 6, 7, 8, 9, 10, 11, 12, 13, 14, or 15 mm.

Translating the first sleeve portion 302 from the distal position 338 to the proximal position 340 causes the flanges 342 to fold and extend radially similarly as described above. Again, the radial length of each flange 342 is approximately half of the length of each flange 342 from the proximal end 344 to the distal end 346 of the flange 342. Thus, for example, for sleeves 300 in which each flange 342 has a radial length of 5 mm when radially expanded, each flange 342 has a length from the proximal end 344 to the distal end 346 of the flange 342 of approximately 10 mm. Likewise, for sleeves 300 in which each flange 342 has a radial length of 10 mm when radially expanded, each flange 342 has a length from the proximal end 344 to the distal end 346 of the flange 342 of approximately 20 mm. This is relevant for reasons as discussed above.

In some embodiments each flange 342 is integral to the first and second sleeve portions 302, 320. This can be advantageous as discussed above.

Also in some embodiments, each flange 342 is attached to the first and second sleeve portions 302, 320. This can be advantageous also as discussed above.

In some embodiments, each flange 342 has a sigmoidal shape. This can be accomplished, for example, by preparing the first sleeve portion 302, the second sleeve portion 320, and the flanges 342 integrally from a piece of semi-rigid film made, for example, from polycarbonate, and using a plotter-cutter to cut the film, as discussed above. Flanges 342 having a sigmoidal shape can be advantageous as discussed above.

In other embodiments, each flange 342 can have other shapes, for example hexagonal shapes, among others.

In some embodiments, each flange 342 has an intermediate portion 354 between the proximal and distal ends 344, 346 of the flange 342 and a width that decreases distally from the proximal end 344 of the flange 342 to the intermediate portion 354 and that increases distally from the intermediate portion 354 to the distal end 346 of the flange 342, as discussed above.

Like the first and second sleeve portions 302, 320, in some embodiments the flanges 342 can be made, for example, from one or more of polyethylene terephthalate glycol, polycarbonate, or polystyrene. This can be advantageous as discussed above.

Thus, in some embodiments the first sleeve portion 302, the second sleeve portion 320, and the plurality of flanges 342 are made from one or more of polyethylene terephthalate glycol, polycarbonate, or polystyrene.

The sleeve 300 also comprises a reversible locking mechanism that can be reversibly actuated to prevent the first sleeve portion 302 from translating away from the second sleeve portion 320 when the first sleeve portion 302 is in the proximal position 340. The reversible locking mechanism also can be used for preventing the sleeve 300 from unintentionally sliding along the surgical port 500. The reversible locking mechanism is not shown in combination with the first sleeve portion 302, the second sleeve portion 320, and the plurality of flanges 342, but can be, for example, a collar, a clamp, or a ratchet mechanism, among other reversible locking mechanisms, as described above.

In some embodiments, the first sleeve portion 302, the second sleeve portion 320, and the flanges 342 are provided free of sharp edges. This also can be advantageous for protecting tissue of a patient from being injured.

The sleeve 300 can be provided as a single use sterile device.

A third system for retention of a surgical port 500 also is provided. The system comprises the third sleeve 300 as described above. The system also comprises a surgical port 500. The second sleeve portion 320 is fixedly secured to the surgical port 500 along the inner surface 330 of the second sleeve portion body 326.

A method of use of the third sleeve 300 in performing a surgery on a patient in need thereof also is provided. The method comprises steps of: (1) securing the third sleeve 300 to a surgical port 500 fixedly along the inner surface 330 of the second sleeve portion body 326; (2) inserting the surgical port 500 and the third sleeve 300 through an incision in a body wall of the patient such that the flanges 342 of the third sleeve 300 extend into a surgical cavity of the patient, wherein during the inserting the first sleeve portion 302 is in the distal position 338 and the flanges 342 are radially collapsed; (3) translating the first sleeve portion 302 from the distal position 338 to the proximal position 340, thereby radially expanding the flanges 342; (4) actuating the reversible locking mechanism to prevent the first sleeve portion 302 from translating away from the second sleeve portion 320; and (5) inserting one or more surgical instruments through the surgical port 500 into the surgical cavity of the patient.

In some embodiments, the method further comprises steps of: (6) withdrawing the one or more surgical instruments from the surgical cavity of the patient through the surgical port 500; (7) releasing the reversible locking mechanism to allow the first sleeve portion 302 to translate away from the second sleeve portion 320; (8) translating the first sleeve portion 302 from the proximal position 340 to the distal position 338, thereby radially collapsing the flanges 342; and (9) withdrawing the surgical port 500 and the third sleeve 300 from the surgical cavity through the incision in the body wall.

EXAMPLES

Example 1: Kite-Shaped Cut Design and Dimensions

A first example approach for making an exemplary first sleeve for retention of a surgical port as disclosed herein, also termed a foldable sleeve, is as follows. With reference to FIGS. 35-38, in accordance with this example the first sleeve portion is a semi-rigid plastic material that fits as a sleeve tightly to a surgical port and has a full length matching that of the surgical port from a distal end of the surgical port to a proximally located back end mount of the surgical port. This can correspond to a length of approximately 120 mm for a standard 8 mm robotic port. The second sleeve portion and the flanges are also made from a semi-rigid plastic material. For the second sleeve portion and the flanges, an initial piece of the material can be cut to form hexagonal flanges extending distally from the second sleeve portion by removing kite-shaped cuts from the initial piece of material. The second sleeve portion fits tightly over the first sleeve portion. The flanges are adhered at their distal ends to the first sleeve portion at its distal end. Optionally, a thin flexible film is applied over the second sleeve portion and the flanges and is adhered at both the distal ends of the first sleeve portion and the flanges and along an outer surface of the second sleeve portion.

Initially, the flanges are reversibly collapsed along the first sleeve portion. By sliding the second sleeve portion distally along the first sleeve portion, the flanges fold to radially expand and form a predetermined collar shape for retention of the surgical port. A snap clamp can then be placed over the first and second sleeve portions, proximally to the back end mount of the surgical port, to maintain the flanges as radially expanded and attach the sleeve to the port. The process can be reversed to radially collapse the flanges.

Figure 35:
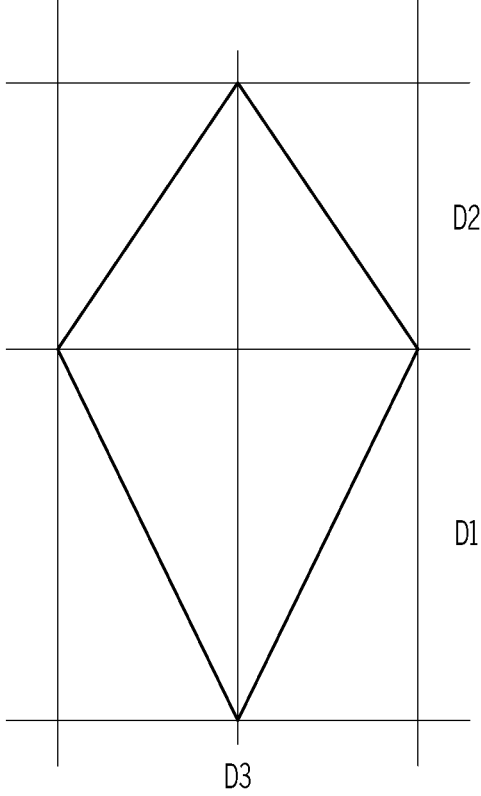
FIG. 35 shows a schematic diagram of a kite-shaped cut of an exemplary first sleeve as described herein, with reference to Example 1. As shown, the kite-shaped cut has a long axis having a length of D1+D2 and a short axis having a length of D3.

The kite-shaped cuts in the initial material for the second sleeve portion and the flanges determine the final shape of the collar. With reference to FIG. 35, the kite-shaped cuts have a long axis having a length of D1+D2, and a short axis having a length of D3. By changing the lengths of D1 and D2, and the ratio between them, the direction of the fold and size of the folded collar are modifiable to obtain a desired final geometry for the collar. The length of D3 and the total number of cuts made equidistantly around the initial material determines the rigidity of the final folded collar and the ease by which the folding mechanism can be deployed.

Figure 36:
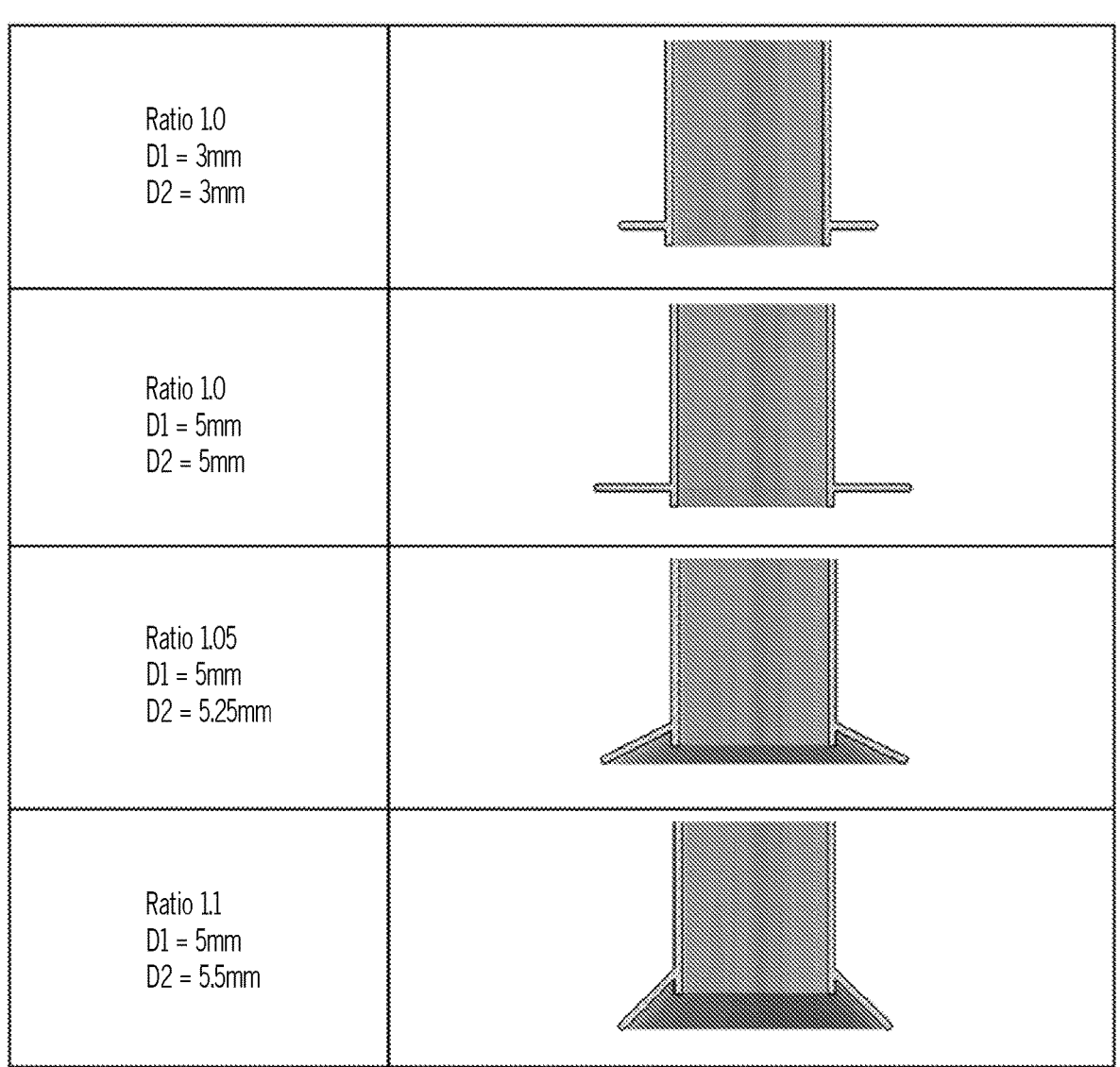
FIG. 36 and FIG. 37 show cross sectional views of the distal ends of a first sleeve portion and a second sleeve portion and a plurality of flanges of a first sleeve as described herein, having a kite-shaped cut design as described in Example 1, in which the flanges are fully radially expanded. The lengths and ratios of D1 and D2 of the kite-shaped cuts are as indicated. The kite-shaped cuts are not shown. The figures illustrate how the dimensions of collars resulting from folding of the flanges can be modified by modifying the ratios of the lengths of D1 and D2 of the kite-shaped cuts.
Figure 37:
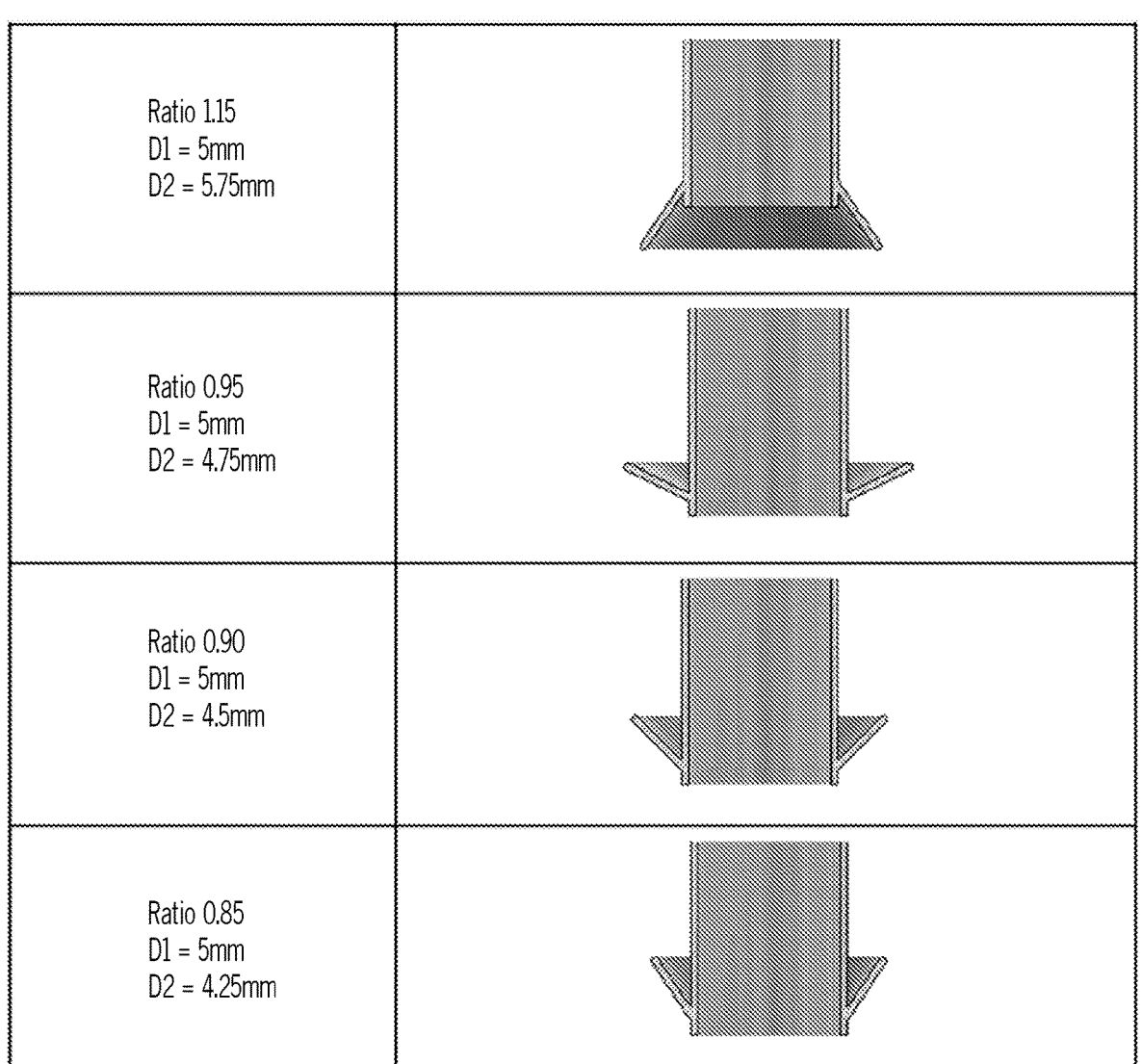

With reference to FIG. 36 and FIG. 37, the ratios of the lengths of D1, D2, and D3 of the kite-shaped cuts can be modified to modify the dimensions of the resulting collars. Cross sections of the sleeve design are shown at varying ratios between D1 and D2. These cross sections demonstrate the folding size and direction of the collar designs at ratios of D2:D1 of 0.85 to 1.15 and lengths of D1 of 3 mm and 5 mm. In FIG. 36 and FIG. 37, the kite-shaped cuts are not shown for cross sectional drawing purposes, and thus dimensions for D3 are not shown or modified in these views.

Figure 38:
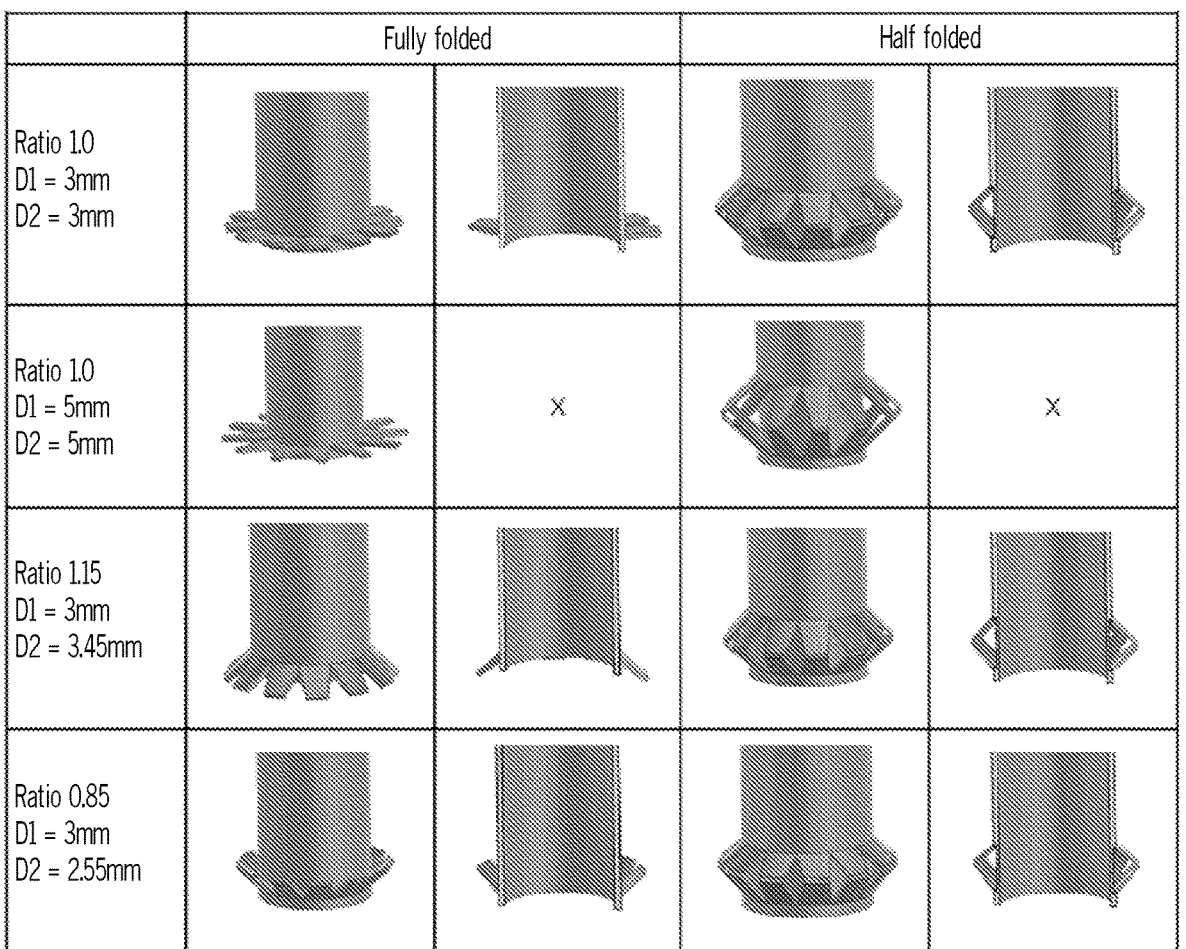
FIG. 38 shows additional cross sectional views of the distal ends of a first sleeve portion and a second sleeve portion and a plurality of flanges of a first sleeve as described herein, having a kite-shaped cut design as described in Example 1, in which the flanges are either fully radially expanded or partially radially expanded. The lengths and ratios of D1 and D2 of the kite-shaped cuts are as indicated. The length of D3 of the kite-shaped cuts is 1 mm.
Figure 42:
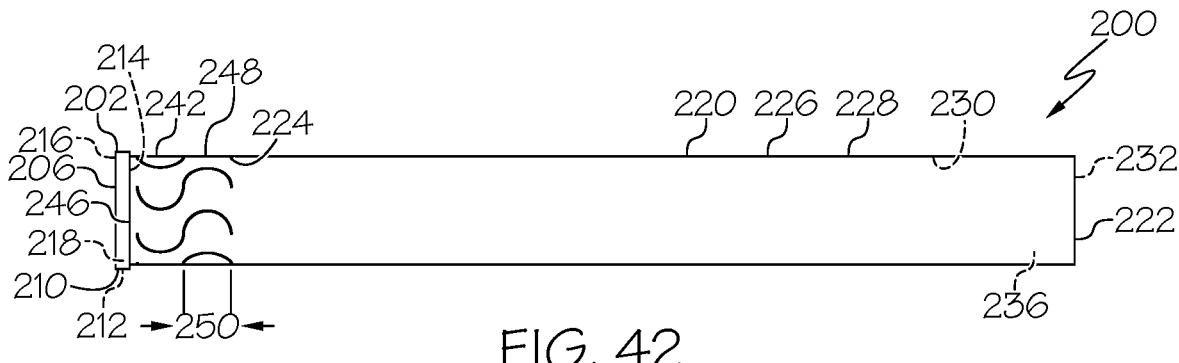
FIG. 42 is a side view of the first sleeve portion, the second sleeve portion, and the plurality of flanges of FIG. 41.
Figure 43:
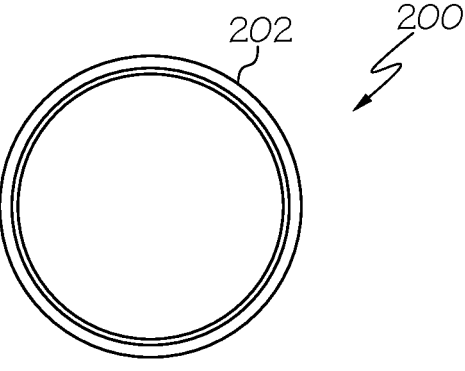
FIG. 43 is a front view of the first sleeve portion, the second sleeve portion, and the plurality of flanges of FIG. 41.
Figure 44:
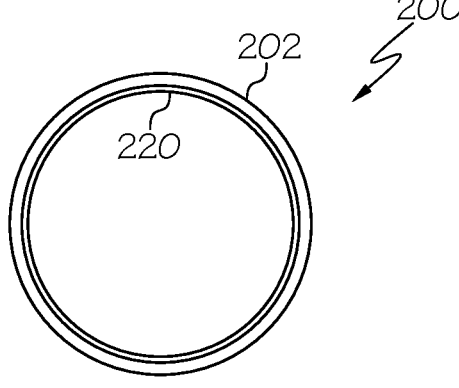
FIG. 44 is a back view of the first sleeve portion, the second sleeve portion, and the plurality of flanges of FIG. 41.

As shown in FIG. 38, in additional views collars are shown fully radially expanded, also termed fully folded, and partially radially expanded, also termed half-folded. In these views, the length of D3 is 1 mm and a total of 12 kite-shaped cuts have been made.

In accordance with this example, the first sleeve portion, second sleeve portion, and flanges can be made from a semi-rigid plastic, with options including polyethylene terephthalate glycol, polycarbonate, or polystyrene. The thin flexible film can be made from silicone or polyurethane. Solvents and adhesives that are compatible with these materials can be used to bond the material layers together. A flexible adhesive can be used. A nonflexible adhesive also may work to the extent that the adhesive will be applied only to non-moving and non-flexing portions of the sleeve.

Example 2: Foldable Sleeve with Sigmoid-Shaped Cuts

A second example approach for making a sleeve for retention of a surgical port as disclosed herein is as follows. With reference to FIG. 19, FIG. 39, and FIG. 40, in accordance with this example the first sleeve portion, the second sleeve portion, and the flanges are made from a cutout of a thin semi-rigid plastic film having a rectangular shape with a long axis and short axis. As shown in FIG. 19, cuts that are initially linear and then sigmoid-shaped are made along the long axis of the cutout, along portions of the cutout that become the second sleeve portion and the flanges, respectively. The remaining portion of the cutout becomes the first sleeve portion. The cutting can be accomplished, for example, by use of a plotter-cutter. Following cutting, the sleeve can be formed by adhering the cutout to itself along its long sides, and then folding the second sleeve portion over the first sleeve portion, such that the second sleeve portion and the flanges cover the first sleeve portion.

Folding lines D1 and D2 are shown on the cutout in FIG. 39.

As shown in FIG. 40, the resulting shape for sigmoid cuts with D1 and D2 having equal lengths results in flanges that form a flare shape when radially expanded.

Like for the example sleeve with the kite-shaped cuts, the example sleeve including the sigmoid-shaped cuts may be modified with respect the lengths of D1 and D2 to change the flare angle upon radial expansion of the flanges.

Other approaches for making foldable sleeves with sigmoid-shaped cuts include, for example, blow molding and overmolding, among other approaches. Blow molding and overmolding would require tooling. Adhesive could be omitted.

Example 3: Foldable Sleeve with Sigmoid-Shaped Cuts

Two example sleeves including sigmoid-shaped cuts were tested within the confines of a live porcine model. The model was an anesthetized live pig, roughly 40 kg. The two examples sleeves were made as described in Example 2, with the details and differences as follows. The two example sleeves included sigmoid-shaped flanges having radial lengths of 5 mm when radially expanded. For the first sleeve, designated PRDa, the flanges were made from a semi-rigid material. For the second sleeve, designated PRDb, the flanges were made from a soft material. Neither sleeve included the optional thin flexible film layer.

The first sleeve, with flanges made from the semi-rigid material, performed better than the second sleeve, with flanges made from the soft material.

With reference to FIGS. 52-62, details and testing of results for the first sleeve were as follows.

Testing setup: The planned set up was to mimic robotic extended totally extraperitoneal repair (eTEP) setup with unilateral side dock. Optical trocar access was obtained into the left retrorectus space. Blunt dissection was used to develop the space. Minimal bleeding was noted. A standard 8 mm skin incision was made for port placement. 5 mm 0-degree and 30-degree scope was used for testing.

Test 1: Sleeve with rigid flange (PRDs): A first robotic port with PRDa placed in the middle port position at the lateral border of the rectus muscle. The port with PRDa was easy to insert through the soft tissues with the flange collapsed. No significant drag was noted. Once in place the PRDa flange was expanded and held the abdominal wall. The flange was flush with the muscle and retracted the tissue. External pulling forces on the port demonstrated the PRDa maintained good position and did not withdraw into the tissues. Previous testing measured 10 newtons (2.25 pound-force) required to pull PRDa with expanded flange through the porcine wall. PRDa remained within the retrorectus space at all steep angles of testing. The material density appeared to be appropriate but the flange size could be increased to greater than 5 mm for additional hold. Pulling on the port provided retraction of the abdominal wall, expanding the overall working space. The flange retracted muscle. No tissue fell over the face of the port even with the port loosely hanging on the abdominal wall. By direct comparison, a standard robotic port demonstrated withdrawal of the standard robotic port back into the abdominal wall and tissue falling over the face of the port. Additionally, loss of instrument function was observed at standard insertion depth using the robotic port, alone. Complete instrument function was obtained in the surgical cavity by PRDa. Port removal was easy without noted trauma or increased force of the PRDa with the flanges collapsed.

Steep angulation at the right upper port did note some retraction of the previously used PRDa through a previously intubated trocar site.

Edges of the flange did not cut through an encased vessel. The flanges ultimately fractured during this testing.

Blood near the flange did not drip directly on the camera within the robotic port but instead flowed around the tip. This should avoid obscuring the camera view from intraoperative bleeding in the vicinity of the camera. This was an unexpected and advantageous result.

An end on view of the PRDa showed good function. The end on view demonstrates blood flowing around the PRDa rather than into the orifice.

Takeaway points include the following.

Flanges having semi-rigid material density performed better than flanges made of soft material in the porcine abdominal wall.

Sigmoid-shaped cut flange design appears to be advantageous.

Increasing flange size from 5 mm to 10 mm may improve retention of surgical port in surgical cavity.

With robotic port retention sleeve continued changes to the depth of the port and trauma from the flanges caused tissue damage and eventually the port would slide through the muscle. Importantly, once affixed to the robotic arm of robotic surgical platform, the large movements would be minimized because the robotic arm is fixed in space around a remote center. Thus, we would not anticipate such large movements in the standard surgical case, and the standard surgical motion would be countered by the retention forces of the sleeve and retain the port in the surgical cavity. Therefore the port would not get reamed out like demonstrated in this porcine model.

Without a thin flexible film, sharp edges of the flanges caused some trauma. Thus, we may consider wrapping the outside of the sleeve with a thin coating or smoothing the edges of the flanges to minimize trauma. Alternatively, using flanges made with sigmoidal cuts in a standard surgical case may be sufficient to avoid such trauma, so long as the flanges do not fracture.

There was no noted gas translocation into the abdominal wall soft tissues from port retraction.

Flanges fractured with repeated use or excess trauma.

Expanded flange does not hang over the opening of the port and therefore does not distort/obscure any part of the camera view.

The invention claimed is:

1. A sleeve for retention of a surgical port comprising:
   (a) a first sleeve portion comprising a proximal end, a distal end, and a first sleeve portion body extending therebetween;
   (b) a second sleeve portion comprising a proximal end, a distal end, and a second sleeve portion body extending therebetween, the second sleeve portion being disposed around the first sleeve portion and being reversibly slidable distally from a first position to a second position along the first sleeve portion;
   (c) a plurality of flanges disposed in a radial sequence around the first sleeve portion adjacent the distal end of the first sleeve portion, each flange having a proximal end, a distal end, and a flange strip extending therebetween, the proximal end of each flange extending from the distal end of the second sleeve portion in the radial sequence, the distal end of each flange extending from the distal end of the first sleeve portion in the radial sequence, and the flanges being radially collapsed along the first sleeve portion when the second sleeve portion is in the first position and being radially expanded around the first sleeve portion when the second sleeve portion is in the second position; and
   (d) a reversible locking mechanism that can be reversibly actuated to prevent the second sleeve portion from sliding along the first sleeve portion when the second sleeve portion is in the second position, wherein:
   the first sleeve portion body has an outer surface, an inner surface, a proximal opening, a distal opening, and a lumen extending between the proximal and distal openings of the first sleeve portion body;
   the second sleeve portion body has an outer surface, an inner surface, a proximal opening, a distal opening, and a lumen extending between the proximal and distal openings of the second sleeve portion body;

the inner surface of the second sleeve portion body is in slidable contact with the outer surface of the first sleeve portion body;

the first sleeve portion is configured for placement of a surgical port through the proximal opening of the first sleeve portion body and into the lumen of the first sleeve portion body to the distal opening of the first sleeve portion body and to be fixedly secured to the surgical port along the inner surface of the first sleeve portion body; and the distal end of the first sleeve portion does not extend distally beyond the distal ends of the flanges when the second sleeve portion is in the first position or the second position.

2. The sleeve according to claim 1, wherein the second sleeve portion is configured for placement of the first sleeve portion within the lumen of the second sleeve portion body through the proximal opening of the second sleeve portion body.

3. The sleeve according to claim 1, wherein the plurality of flanges consists of 5 to 25 flanges.

4. The sleeve according to claim 1, wherein each flange has a radial length of 1 to 15 mm when radially expanded around the first sleeve portion.

5. The sleeve according to claim 1, wherein each flange is integral to the first and second sleeve portions.

6. The sleeve according to claim 1, wherein each flange is attached to the first and second sleeve portions.

7. The sleeve according to claim 1, wherein each flange has a sigmoidal shape.

8. The sleeve according to claim 1, wherein each flange has an intermediate portion between the proximal and distal ends of the flange and a width that decreases distally from the proximal end of the flange to the intermediate portion and that increases distally from the intermediate portion to the distal end of the flange.

9. The sleeve according to claim 1, wherein the first sleeve portion, the second sleeve portion, and the plurality of flanges are made from one or more of polyethylene terephthalate glycol, polycarbonate, or polystyrene.

10. The sleeve according to claim 1, further comprising a flexible film covering the second sleeve portion and the plurality of flanges, the flexible film being adhered to the first sleeve portion at the distal end of the first sleeve portion and to the second sleeve portion along the outer surface of the second sleeve portion body, and the flexible film not being adhered to the plurality of flanges.

11. A system for retention of a surgical port comprising:

(a) the sleeve according to claim 1; and (b) a surgical port, wherein:

the first sleeve portion is fixedly secured to the surgical port along the inner surface of the first sleeve portion body.

12. A method of use of the sleeve of according to claim 1 in performing a surgery on a patient in need thereof, the method comprising steps of:

(1) securing the sleeve to a surgical port fixedly along the inner surface of the first sleeve portion body;

(2) inserting the surgical port and the sleeve through an incision in a body wall of the patient such that the flanges of the sleeve extend into a surgical cavity of the patient, wherein during the inserting the second sleeve portion is in the first position and the flanges are radially collapsed along the first sleeve portion;

(3) sliding the second sleeve portion from the first position to the second position, thereby radially expanding the flanges around the first sleeve portion;

(4) actuating the reversible locking mechanism to prevent the second sleeve portion from sliding along the first sleeve portion; and (5) inserting one or more surgical instruments through the surgical port into the surgical cavity of the patient.

13. The method according to claim 12, the method further comprising steps of:

(6) withdrawing the one or more surgical instruments from the surgical cavity of the patient through the surgical port;

(7) releasing the reversible locking mechanism to allow the second sleeve portion to slide along the first sleeve portion;

(8) sliding the second sleeve portion from the second position to the first position, thereby radially collapsing the flanges along the first sleeve portion; and (9) withdrawing the surgical port and the sleeve from the surgical cavity through the incision in the body wall.

* * * * *